United States Patent
Greiser et al.

(10) Patent No.: US 11,304,653 B2
(45) Date of Patent: Apr. 19, 2022

(54) MAGNETIC RESONANCE IMAGING SYSTEM WITH A ROTATABLE MAGNET

(71) Applicant: Siemens Healthcare GmbH, Erlangen (DE)

(72) Inventors: Andreas Greiser, Erlangen (DE); Rene Kartmann, Nuremberg (DE); Stephan Biber, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 17/101,539

(22) Filed: Nov. 23, 2020

(65) Prior Publication Data

US 2021/0156938 A1 May 27, 2021

Related U.S. Application Data

(60) Provisional application No. 62/941,140, filed on Nov. 27, 2019, provisional application No. 62/941,268, (Continued)

(51) Int. Cl.
*G01R 33/385* (2006.01)
*A61B 5/055* (2006.01)
(Continued)

(52) U.S. Cl.
CPC ............ *A61B 5/4547* (2013.01); *A61B 5/055* (2013.01); *G01R 33/34084* (2013.01); *G01R 33/3802* (2013.01); *G01R 33/3858* (2013.01)

(58) Field of Classification Search
CPC .......... G01R 33/3858; G01R 33/34084; G01R 33/3802; G01R 33/3808; G01R 33/445; A61B 5/055; A61B 5/4547
See application file for complete search history.

(56) References Cited

U.S. PATENT DOCUMENTS

| 6,570,383 B1 | 5/2003 | McKinnon et al. |
| 2009/0230961 A1 | 9/2009 | Viswanathan |

(Continued)

FOREIGN PATENT DOCUMENTS

| EP | 3349029 A1 | 7/2018 |
| WO | 2010142760 A2 | 12/2010 |
| WO | 2019200159 A1 | 10/2019 |

OTHER PUBLICATIONS

Kegler C., et al.: "Prepolarized Fast Spin-Echo Pulse Sequence for Low-Field MRI"; Magnetic Resonance in Medicine 57:1180-1184; 2007.
(Continued)

*Primary Examiner* — Susan S Lee
(74) *Attorney, Agent, or Firm* — Banner & Witcoff, Ltd.

(57) ABSTRACT

A magnetic resonance imaging system can include a magnetic field generator, an image acquisition region and a radiofrequency system including at least one radiofrequency antenna. The radiofrequency system can emit a radiofrequency excitation pulse into the image acquisition region and receive magnetic resonance signals from the image acquisition region. The magnetic field generator can include at least one magnet to generate a magnetic field in the image acquisition region, a magnet holder to carry the at least one magnet and a rotation system to position the magnet holder along a rotation trajectory.

18 Claims, 7 Drawing Sheets

Figure 1:
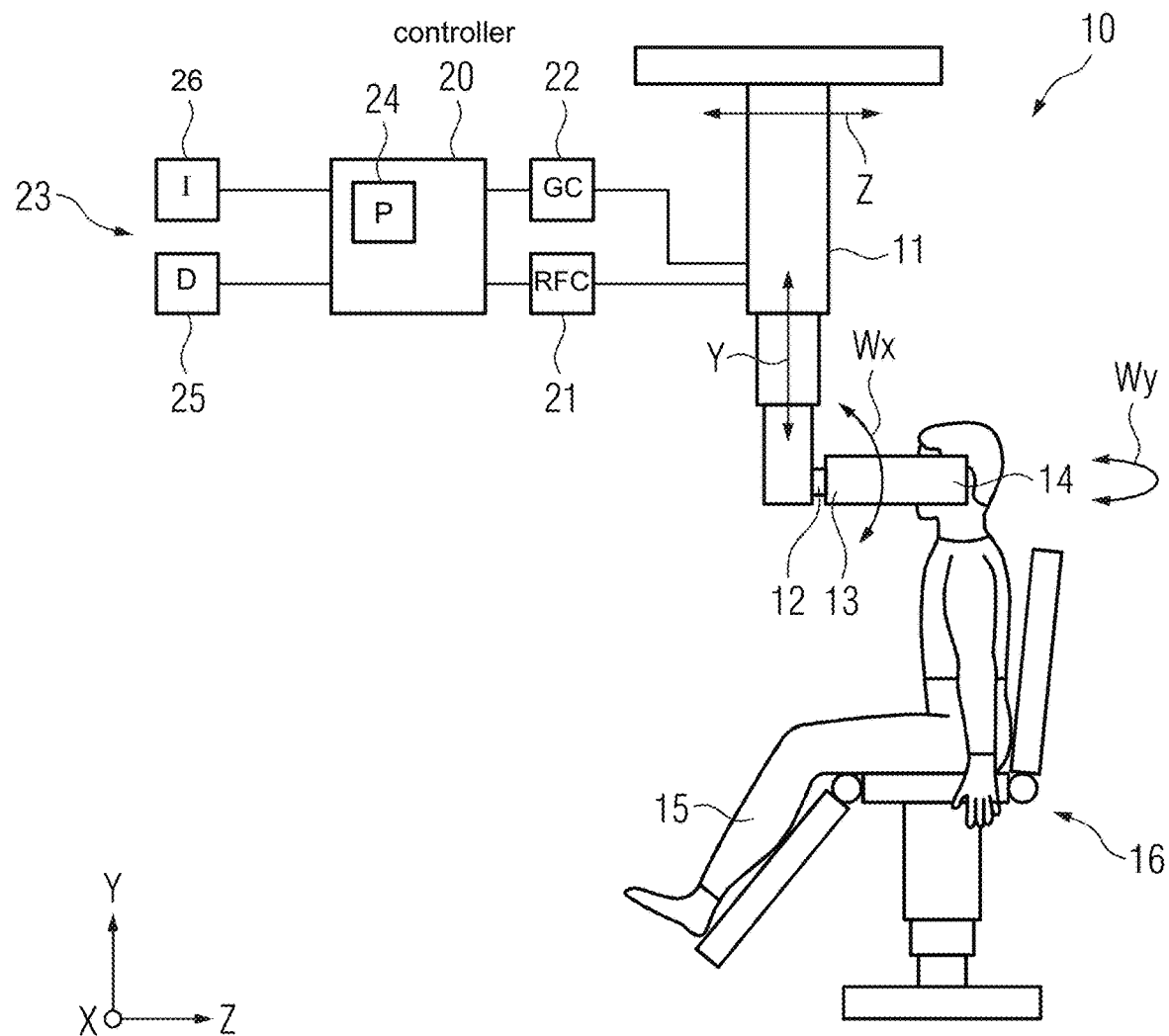

Related U.S. Application Data filed on Nov. 27, 2019, provisional application No. 62/941,348, filed on Nov. 27, 2019.

(51) Int. Cl.
*A61B 5/00* (2006.01)
*G01R 33/34* (2006.01)
*G01R 33/38* (2006.01)

(56) References Cited

U.S. PATENT DOCUMENTS

| | | |
|---|---|---|
| 2014/0111202 A1 | 4/2014 | Wald et al. |
| 2016/0313420 A1 | 10/2016 | Rasche et al. |
| 2018/0199853 A1 | 7/2018 | Abkai et al. |
| 2018/0224512 A1 | 8/2018 | Poole et al. |
| 2021/0031055 A1 | 2/2021 | Jiang et al. |
| 2021/0158563 A1* | 5/2021 | Rinck .................. G06T 7/70 |

OTHER PUBLICATIONS

European Search Report dated Apr. 1, 2021, EP Application No. 20202953.4.

European search report dated Jul. 26, 2021, Application No. 20202953.4.

\* cited by examiner

MAGNETIC RESONANCE IMAGING SYSTEM WITH A ROTATABLE MAGNET

CROSS REFERENCE TO RELATED APPLICATIONS

This patent application claims priority to, and the benefit of: U.S. Provisional Patent Application No. 62/941,268, filed Nov. 27, 2019; U.S. Provisional Patent Application No. 62/941,348, filed Nov. 27, 2019; and U.S. Provisional Patent Application No. 62/941,140, filed Nov. 27, 2019, each of which is incorporated herein by reference in its entirety.

BACKGROUND

Field

Diseases of the teeth and the periodontium, such as caries or periodontitis, are typically diagnosed with X-ray-based imaging methods. For this purpose, conventional or digital X-ray projection methods, and recently also three-dimensional X-ray methods, are used. An example of a three-dimensional X-ray method is digital volume tomography, which can be used for imaging of the teeth and the viscerocranium.

Related Art

A major disadvantage of X-ray-based imaging methods is the application of ionizing radiation for imaging. Magnetic resonance tomography is an imaging method that avoids ionizing radiation. Furthermore, magnetic resonance tomography typically provides an enhanced soft tissue contrast in comparison to X-ray-based imaging methods and natively supports three-dimensional imaging of an examination object. Thus, magnetic resonance tomography represents a potential alternative to known X-ray methods for imaging teeth and/or jaws of the examination object as well as diagnosing dental diseases.

Magnetic resonance tomography represents a prominent imaging method for acquiring images of an interior of the examination object. In order to carry out a magnetic resonance measurement, the examination object is positioned in a strong and homogeneous static magnetic field (BO field) of a magnetic resonance device. The static magnetic field may comprise magnetic field strengths of 0.2 Tesla to 7 Tesla in order to align nuclear spins of the examination object along the static magnetic field. For triggering so-called nuclear spin resonances, radiofrequency excitation pulses are emitted into the examination subject. Each radiofrequency excitation pulse causes a magnetization of nuclear spins within the examination object to deviate from the static magnetic field by an amount which is known as the flip angle. A radiofrequency excitation pulse may comprise an alternating magnetic field with a frequency which corresponds to the Larmor frequency at the respective static magnetic field strength. Excited nuclear spins may exhibit a rotating and decaying magnetization (nuclear magnetic resonance), which can be detected using dedicated radiofrequency antennas. For spatial encoding of measured data, rapidly switched magnetic gradient fields are superimposed on the static magnetic field.

The received nuclear magnetic resonances are typically digitized and stored as complex values in a k-space matrix. This k-space matrix can be used as a basis for the reconstruction of magnetic resonance images and for determining spectroscopic data. A magnetic resonance image is typically reconstructed by means of a multi-dimensional Fourier transformation of the k-space matrix.

In avoiding ionizing radiation, magnetic resonance tomography is particularly suitable for continuous or repetitious diagnostic monitoring of dental diseases and/or tooth development, for example within the framework of a longitudinal imaging study. Longitudinal imaging studies may comprise carrying out a plurality of imaging examinations in order to determine a progression of a disease or a success of a therapeutic treatment over a predetermined period of time. Disadvantages usually associated with magnetic resonance tomography are an extensive space requirement and high equipment costs. These downsides may impede utilization of magnetic resonance tomography for dental imaging applications and the advantages associated with it.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 2:
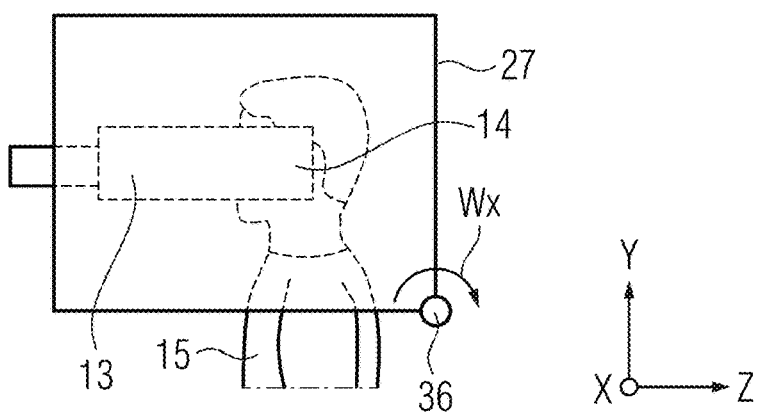
Figure 3:
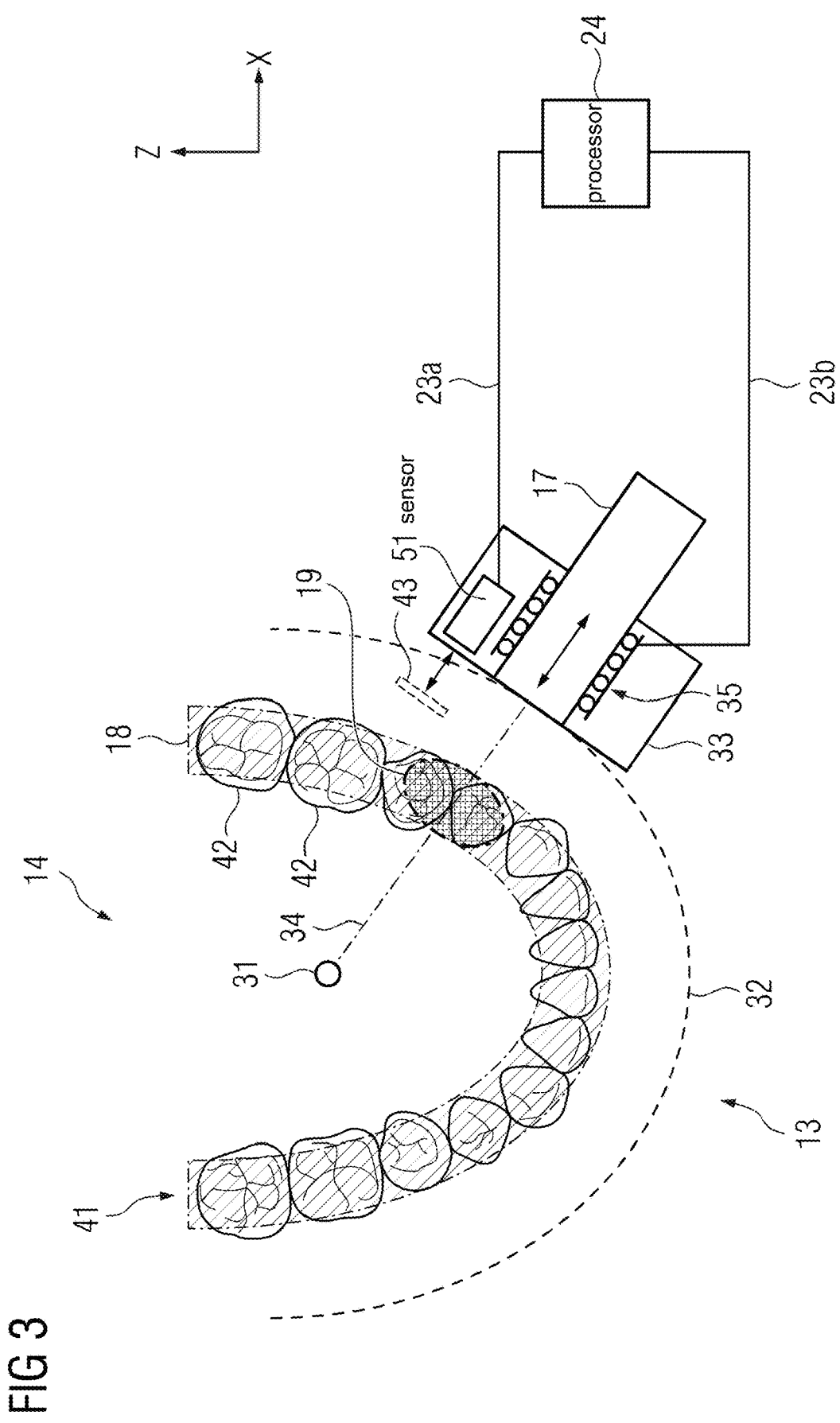
Figure 4:
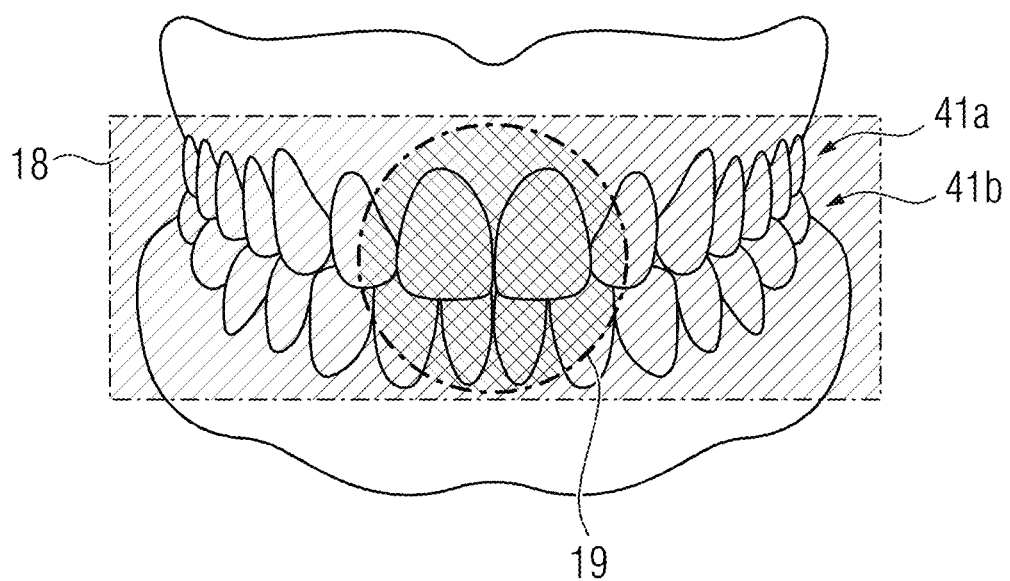
Figure 5:
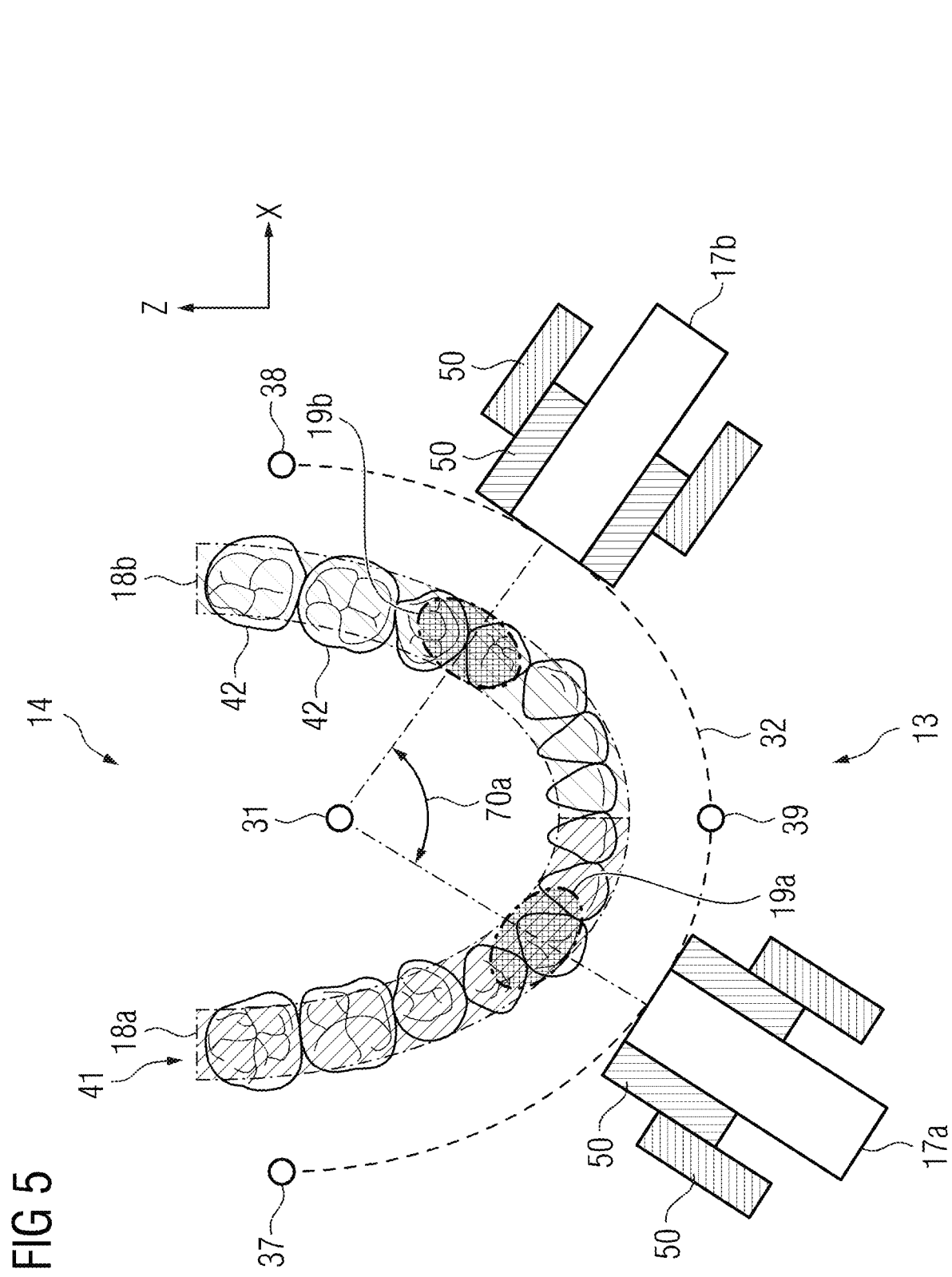
Figure 6:
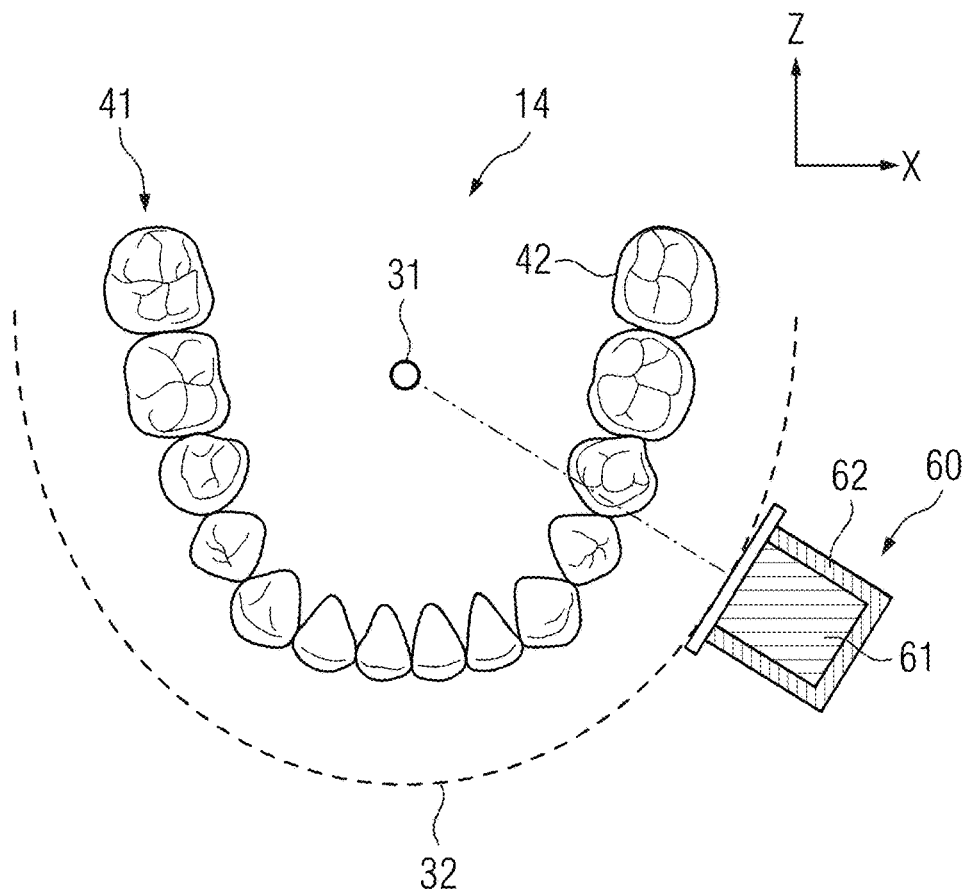
Figure 7:
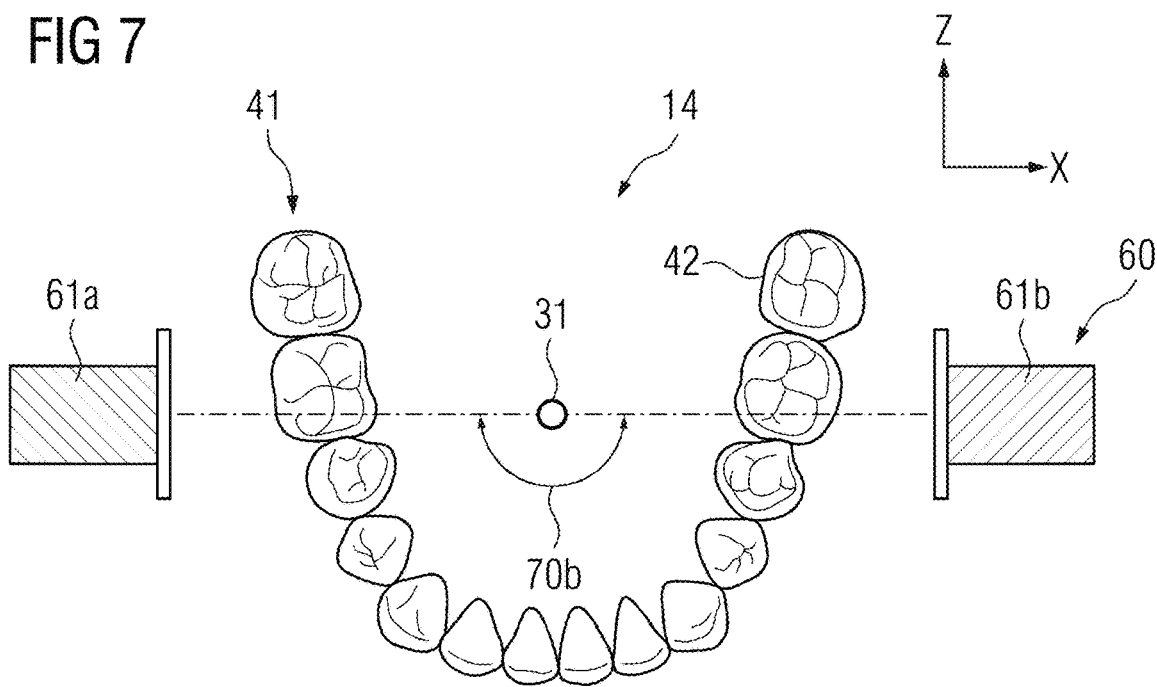
Figure 8:
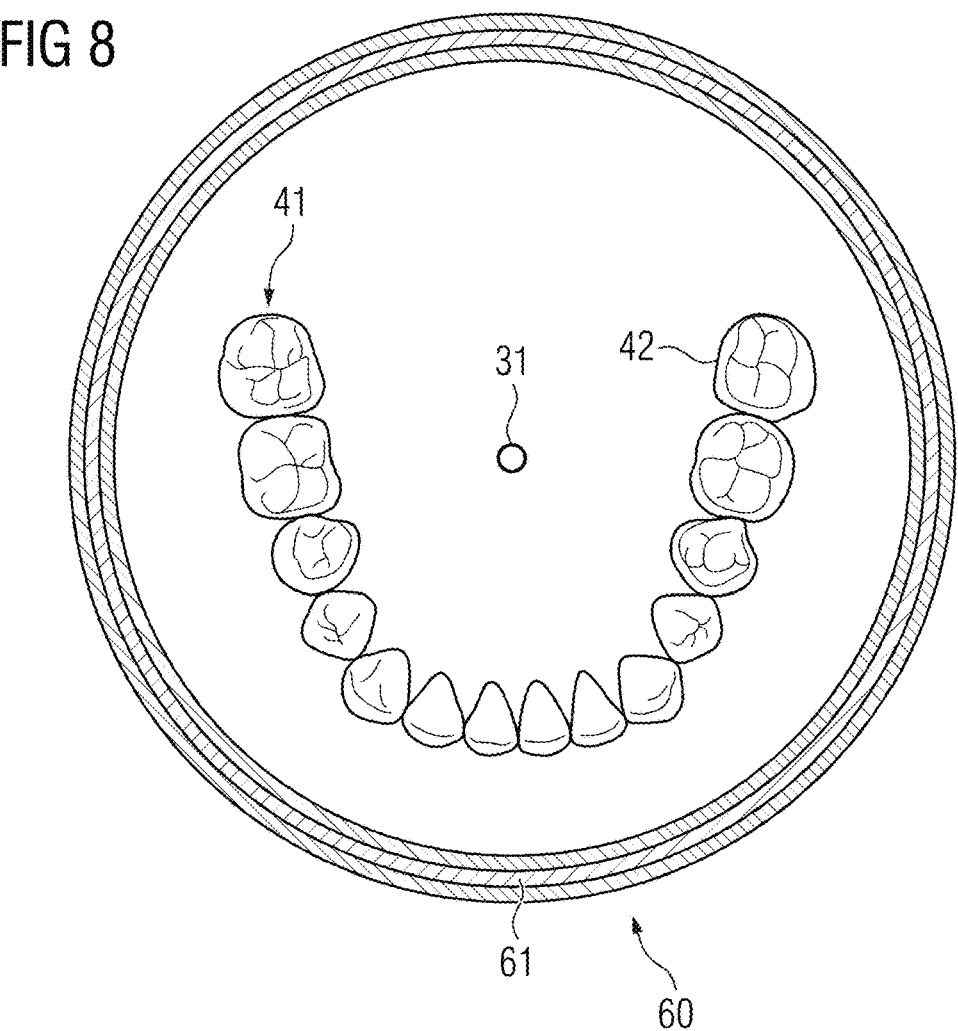
Figure 9:
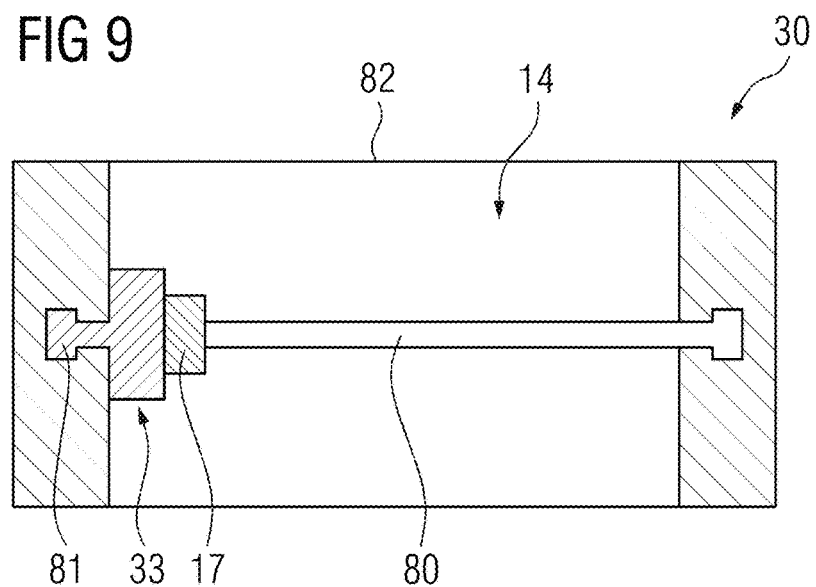
Figure 10:
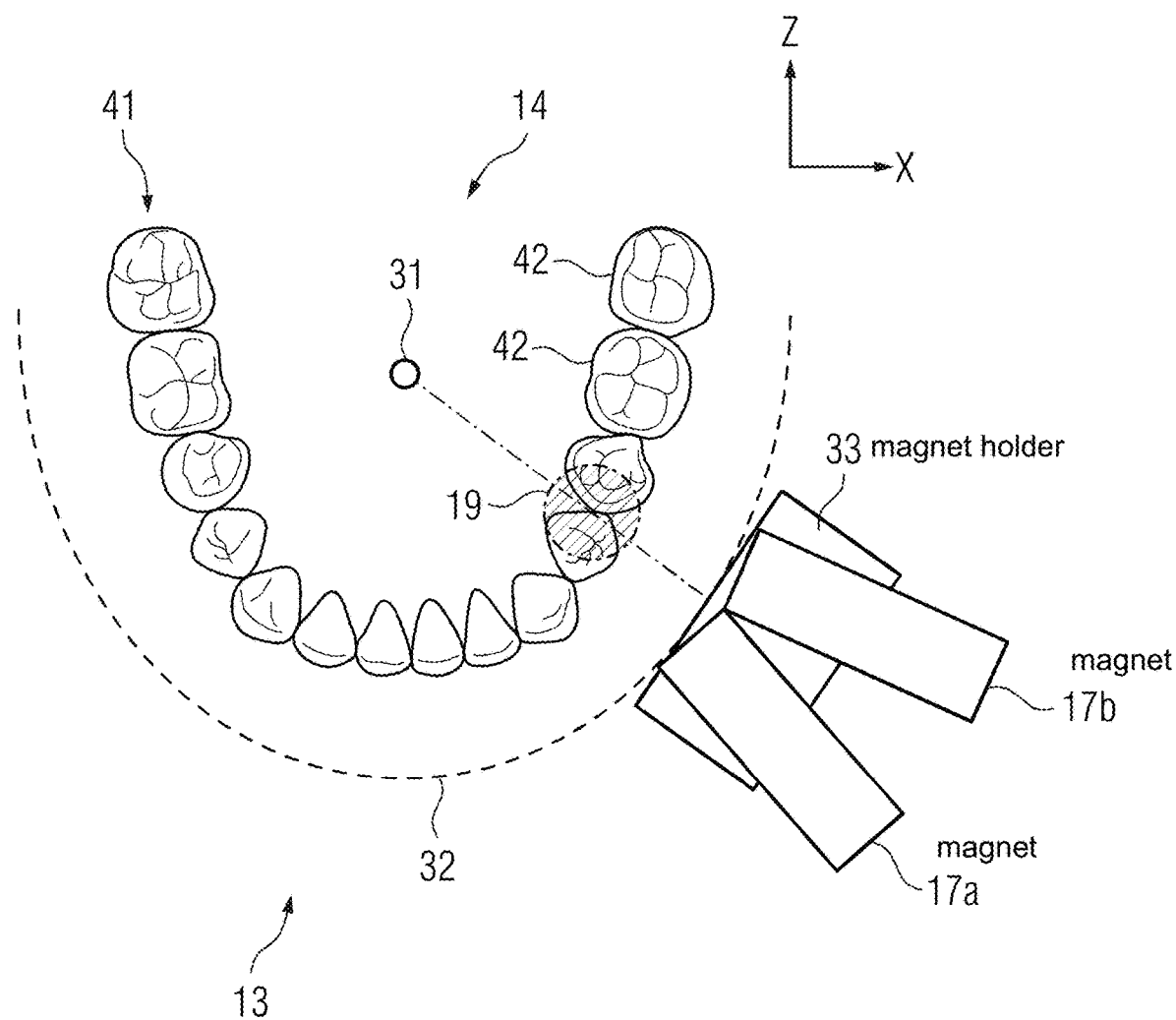

FIG. 1 a schematic representation of a magnetic resonance imaging system according to a first embodiment of the disclosure, FIG. 2 a schematic representation of a housing of the magnetic resonance imaging system according to a second embodiment of the disclosure, FIG. 3 a schematic representation of a magnetic field generator of a magnetic resonance imaging system according to a third embodiment of the disclosure, FIG. 4 a schematic representation of an imaging region of the magnetic resonance imaging system according to a third embodiment of the disclosure, FIG. 5 a schematic representation of a magnetic field generator of a magnetic resonance imaging system according to a fourth embodiment of the disclosure, FIG. 6 a schematic representation of a magnetic field gradient system of a magnetic resonance imaging system according to a fifth embodiment of the disclosure, FIG. 7 a schematic representation of a magnetic field gradient system of a magnetic resonance imaging system according to a sixth embodiment of the disclosure, FIG. 8 a schematic representation of a magnetic field gradient system of a magnetic resonance imaging system according to a seventh embodiment of the disclosure, FIG. 9 a schematic representation of a mechanical guiding rail of a rotation system according to an eight embodiment of the disclosure, FIG. 10 a schematic representation of a magnetic resonance imaging system according to a ninth embodiment of the disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the disclosure is to reduce costs and spatial requirements associated with magnetic resonance imaging systems for imaging of dedicated body regions of a patient.

This object is achieved by a magnetic resonance imaging system according to the disclosure.

The inventive magnetic resonance imaging system comprises a magnetic field generator, an image acquisition region and a radiofrequency system including at least one radiofrequency antenna, wherein the radiofrequency system is configured to emit a radiofrequency excitation pulse into the image acquisition region and receive magnetic resonance signals from the image acquisition region. The magnetic field generator comprises at least one magnet configured to generate a magnetic field in the image acquisition region, a magnet holder configured to carry the at least one magnet and a rotation system configured to position the magnet holder along a rotation trajectory.

The magnetic resonance imaging system may comprise a housing in which the rotation system, the magnet holder and the at least one magnet may be positioned in. The housing may comprise a transparent, a semi-transparent or an opaque material. It is conceivable, that the magnetic resonance imaging system and/or the housing comprise a protective cover positioned in a space between the rotation system and a surface of an examination object. The protective cover may be configured to protect the examination object from moving parts of the rotation system, such as the magnet holder and/or the at least one magnet. The examination object may be a body of a patient and/or a body region of the patient. In an exemplary embodiment, the housing further comprises an electric conductor configured to shield the image acquisition region from electromagnetic interference.

The magnetic resonance system may comprise a support structure configured to adjust a position and/or an orientation of the magnetic field generator and/or to align the at least one magnet with an imaging region of the examination object. An imaging region may be a diagnostically relevant volume of the patient, for example a volume comprising a heart, an eye, a tooth, multiple teeth, a dental arch or other (parts of) organs. In one example, the support structure may comprise an adjustment mechanism, such as a swivel joint, a rotating joint or the like, to adjust an orientation of the magnetic field generator with respect to the examination object. In another example, the support structure may comprise a telescope system and/or a rail system to adjust a height and/or a distance of the magnetic field generator with respect to the examination object. The support structure and/or the adjustment mechanism may provide for at least two degrees of motion, at least three degrees of motion, at least four degrees of motion or at least five degrees of motion of the magnetic field generator.

The image acquisition region may represent a volume wherein the examination object is positioned in order to perform a magnetic resonance imaging examination of the examination object. The image acquisition region typically is at least partially encompassed by the magnetic field generator. For example, the image acquisition region may be confined by the magnetic field generator in at least one spatial direction, at least two spatial directions or at least three spatial directions. It is also conceivable, that the image acquisition region is encompassed by the magnetic field generator in a circumferential direction. The magnetic resonance imaging system may comprise an opening configured to provide an entry to the image acquisition region. The opening may comprise any shape or geometry suitable for receiving an examination object. It is also conceivable, that the housing comprises an opening, such as a circular hole or an oval hole, in order to provide access of the body and/or the body region of the patient to the image acquisition region.

The rotation system may comprise an arc-shaped element. An outline of the arc-shaped element may correspond to at least a section of a perimeter of a circle or an oval. The rotation system may further comprise a rotation center which may represent a center of a circle or oval circumscribing the outline of the arc-shaped element. The rotation trajectory may extend along at least a section of the arc-shaped element of the rotation system. It is conceivable, that the opening of the magnetic resonance imaging system is provided by an opening in the arc-shaped element of the rotation system, thus enabling the examination object to enter the image acquisition region.

A motion of the magnet holder carrying the at least one magnet along the rotation trajectory may result in a relative motion between the magnetic field generated by the at least one magnet and the rotation center. In an exemplary embodiment, the rotation system comprises a motor configured to position the magnet holder along the rotation trajectory. The motor may comprise any kind of drive system, for example an electric, a hydraulic and/or a pneumatic actuator, configured to move the magnet holder along the rotation trajectory. In one embodiment, the motor of the rotation system is configured to move the magnet holder along the rotation trajectory in a continuous fashion. However, the motor may also be configured to move the magnet holder in a step-by-step fashion, e. g. remaining in one position on the rotation trajectory for a time interval of several milliseconds, several seconds or several minutes before moving to a next position on the rotation trajectory. The motion of the magnet holder along the rotation trajectory may cause a corresponding motion of the magnetic field within the image acquisition region of the magnetic resonance imaging device.

The magnet holder may be any kind of structure configured to carry the at least one magnet. In an exemplary embodiment, the at least one magnet is reversibly mounted on the magnet holder via any kind of locking and/or frictional connection. For example, the connection between the at least one magnet and the magnet holder may be realized via a fastener mechanically joining the magnet holder and the at least one magnet. However, the at least one magnet may also be materially bonded to the magnet holder, for example via use of an adhesive.

The at least one magnet of the magnetic field generator may be configured to provide a static magnetic field in the image acquisition region over a predetermined time period. In one embodiment, the magnetic field provided by the at least one magnet may be constant over a time period of a few milliseconds to a few seconds. In another embodiment, the magnetic field provided by the at least one magnet may be constant over a time period of several days, several months or several years. The static magnetic field provided by the at least one magnet is typically defined as the BO magnetic field.

The magnetic resonance imaging system is configured to acquire magnetic resonance imaging data from an examination object positioned in the image acquisition region. In order to do so, the magnetic resonance imaging system may comprise further components usually required for performing a magnetic resonance imaging examination and for processing acquired magnetic resonance imaging data. In particular, the magnetic resonance imaging system may comprise a processor which may be configured to reconstruct a magnetic resonance image from magnetic resonance signals acquired from the image acquisition region.

By providing a magnetic resonance imaging system according to the disclosure, costs and/or spatial requirements associated with conventional magnetic resonance imaging systems can advantageously be reduced.

In one embodiment of the inventive magnetic resonance imaging system, the magnetic field generator comprises a permanent magnet. In one example, the at least one magnet may be a permanent magnet. The use of a permanent magnet may favorably avoid costs and space required for cooling equipment usually associated with superconducting magnets and electromagnets. The permanent magnet may consist of any suitable magnetic material such as AlNiCo (aluminum-nickel-cobalt), NeFeB (neodymium-iron-boron), or SmCo (samarium-cobalt) alloys. The permanent magnet may comprise any desired shape.

In one embodiment, the permanent magnet comprises a bar shape. A bar shape may include a cuboid bar shape, a cylindrical bar shape or a bar shape with a polygonal cross-section, such as a prism. Bar-shaped permanent magnets provide a low-cost solution for generating a magnetic field within the image acquisition region. Furthermore, bar-shaped permanent magnets may favorably be oriented in a direction of the examination object while moving the at least one magnet along the rotation trajectory of the rotation system.

In a further embodiment, the permanent magnet comprises a C-shaped form and two magnetic poles positioned at two opposing ends of the C-shaped form. A C-shaped permanent magnet may favorably increase the magnetic field homogeneity in a region close to the two magnetic poles of the at least one permanent magnet.

In another embodiment of the inventive magnetic resonance imaging system, the magnetic field generator comprises an electromagnet. In one example, the at least one magnet may be an electromagnet. The electromagnet may comprise an electrical conductor wound around a magnetic core made of, for example, a ferromagnetic or ferrimagnetic material. The magnetic core of the electromagnet may comprise a cylindrical shape, a C-shape, a cuboid shape or any other desirable shape. By using an electromagnet, the magnetic field strength can be favorably increased in comparison to a permanent magnet of comparable size. Higher magnetic field strengths can advantageously enhance a quality and/or a signal-to-noise ratio of a magnetic resonance image acquired via the magnetic resonance imaging system.

In still a further embodiment of the inventive magnetic resonance imaging system, the magnetic field generated by the at least one magnet projects from a face of the poles of the at least one magnet in such way that an imaging volume provided by the at least one magnet is situated in front of the face of the poles. An imaging volume may be positioned inside the image acquisition region of the magnetic resonance imaging device and may be moved with respect to the rotation center, when the magnet holder is moved along the rotation trajectory. The imaging volume may be characterized by a particularly homogenous magnetic field. However, it is also conceivable, that the imaging volume is characterized by an approximately linear magnetic field gradient. A size of the imaging volume may coincide with a size of the magnetic field provided by the at least one magnet. However, the size of the imaging volume may also be significantly smaller than the size of the magnetic field. In an exemplary embodiment, the at least one magnet is oriented in such a way, that the imaging volume overlaps with at least a part of the imaging region comprising a diagnostically relevant area or volume within the examination object. The imaging volume may be positioned in proximity to a face of the pole of the at least one magnet oriented approximately in the direction of the rotation center. In an exemplary embodiment, a distance between the imaging volume and the face of the pole oriented in the direction of the rotation center may be less than 5 cm, less than 4 cm or more specifically less than 3 cm. Thus, when moving the at least one magnet along the rotation trajectory, the imaging volume can advantageously be moved along a diagnostically relevant volume of the examination object. Furthermore, costs and/or spatial requirements associated with stronger magnets capable of providing an imaging volume in a greater distance to the at least one magnet can favorably be avoided.

In an exemplary embodiment, the magnetic field generated by the at least one magnet comprises a magnetic field strength in the range of 0.01 to 1.5 Tesla, and more specifically in the range of 0.3 to 1.0 Tesla. By using smaller magnets in close proximity to the examination object, costs and/or spatial requirements related to the magnetic field generator can favorably be reduced.

In one embodiment of the magnetic resonance imaging system, the at least one magnet is configured to generate a substantially homogeneous magnetic field in the image acquisition region. A volume within the image acquisition region, wherein the magnetic field is particularly homogenous, may be an isocenter. The isocenter may represent at least a part of the imaging volume. However, the isocenter may also coincide with the imaging volume. A shape of the isocenter may be represented by a sphere, an ovoid, a cuboid, a prism, a star or any combination of these shapes. It is conceivable, that a diameter of a sphere with the same volume as the isocenter may range between 0.5 cm and 5 cm, 5 cm and 10 cm, 10 cm and 15 cm or 15 cm and 20 cm. In an exemplary embodiment, the diameter of a sphere with the same volume as the isocenter is smaller than 4 cm. The isocenter may be positioned anywhere in the image acquisition region. However, in an exemplary embodiment, the isocenter is positioned in close proximity to a pole face of the at least one magnet as descried above. The magnetic field generated by the at least one magnet may be configured in such way, that two arbitrarily chosen points in the isocenter differ in magnetic field strength by less than 1 ppm (part per million), less than 5 ppm, less than 10 ppm, less than 15 ppm or less than 20 ppm. The at least one magnet may comprise any shape or geometry required for providing the substantially homogeneous magnetic field in the image acquisition region. The provision of the substantially homogeneous magnetic field may advantageously increase a quality of magnetic resonance images provided by the magnetic resonance system.

In a further embodiment of the magnetic resonance imaging system, the at least one magnet is configured to generate an inhomogeneous magnetic field in the image acquisition region, wherein the inhomogeneous magnetic field comprises a magnetic field gradient along a radial direction of the rotation trajectory. A radial direction may be characterized by a vector extending from an arbitrary point on the rotation trajectory to the rotation center of the rotation system. It is conceivable, that the magnetic field strength of the magnetic field provided by the at least one magnet decreases in a direction towards to the rotation center. For example, the strength of the magnetic field may decrease in a linear fashion, a hyperbolic fashion, an exponential fashion or in any other fashion. The vector may also be divided into segments, each characterized by an approximately linearly, hyperbolically or exponentially decreasing magnetic field strength. The inhomogeneous magnetic field of the at least one magnet may represent a known characteristic of the at least on magnet, which may be taken into account during acquisition of magnetic resonance signals, spatial encoding of magnetic resonance signals and/or reconstruction of magnetic resonance images.

In one embodiment, the processor of the magnetic resonance imaging system is configured to perform a spatial encoding of magnetic resonance signals acquired from the image acquisition region in dependence of the magnetic field gradient along the radial direction of the rotation trajectory. For this purpose, a slice of an imaging volume provided by the at least one magnet within the image acquisition region may be excited via a selective radiofrequency excitation pulse provided by the radiofrequency antenna. The selective radiofrequency excitation pulse may comprise a frequency corresponding to a Larmor frequency of a subset of nuclear spins within the magnetic gradient field gradient. In dependence of a known characteristic of the at least one magnet, such as the magnetic field gradient along the radial direction of the rotation trajectory, magnetic resonance signals acquired from the excited slice may be assigned to specific locations between the at least one magnet and the rotation center. By using a magnet which provides an inhomogeneous magnetic field, costs and/or spatial requirements usually associated with higher field homogeneity can favorably be reduced. Furthermore, an inhomogeneous magnetic field may replace at least one magnetic field gradient of a magnetic field gradient system commonly employed to provide a means for spatial encoding of magnetic resonance signals from an imaging volume. Thus, costs and spatial requirements can be reduced in comparison to conventional magnetic resonance imaging system.

In a further embodiment of the magnetic resonance imaging system, the rotation system comprises a mechanical guiding rail which is configured to guide the magnet holder along the rotation trajectory around the rotation center. The mechanical guiding rail may be positioned on the arc-shaped element of the rotation system. A shape and/or a curvature of the mechanical guiding rail may correspond to a shape and/or curvature of the rotation trajectory. In an exemplary embodiment, the mechanical guiding rail comprises a profile, such as a C-profile or a T-profile, which is configured to interlock with a carrier element carrying the magnet holder. However, the mechanical guiding rail may also comprise a simple bar, providing an edge or a ridge which may be at least partially encompassed by the carrier element. The carrier element may be guided along the rotation trajectory via the mechanical guiding rail. In an exemplary embodiment, the carrier element and/or the mechanical guiding rail comprise bearings, such as ball bearings, in order to reduce friction between the carrier element and the mechanical guiding rail. As described above, in an exemplary embodiment, the rotation system comprises a motor configured to move the carrier element and the magnet holder on the mechanical guiding rail along the rotation trajectory. The mechanical guiding rail may limit the motion of the magnet holder to a line along rotation trajectory. Thus, an accuracy and/or a reproducibility of motion of the magnet, as well as a traceability of a position of the at least one magnet along the rotation trajectory can be favorably enhanced.

In one embodiment of the magnetic resonance imaging system, the rotation trajectory comprises a rotation angle in the range of 120° to 270°, and more specifically in the range of 90° to 240°. The rotation angle may define how much of a circumference of the examination object is encompassed by the rotation system. For particular imaging applications, as for example imaging of an eye region, a jaw region or a breast region of a patient, it would just be required to move the at least one magnet along one side of the examination object in order to acquire magnetic resonance signals from these regions. However, particularly in dental imaging, it may be relevant to also image the regions from the sides in order to enhance coverage of these regions via the imaging volume. Thus, the rotation trajectory of the magnet holder may encompass the patient by more than 180°. In an exemplary embodiment, the rotation angle is lower than 270°. A missing section of the circumference of the rotation trajectory may correspond to the opening which enables the patient to access the image acquisition volume. In one embodiment, the examination object may be turned or rotated inside the image acquisition volume either continuously or in discrete steps to acquire magnetic resonance signals from an entire circumferential volume of the patient. Reducing the extent of the rotation trajectory may reduce a size of the rotation system, thus decreasing costs and/or spatial requirements of the magnetic resonance imaging system. Furthermore, providing a half-open rotation system encompassing a rotation angle in the range of approximately 90° to 240° instead of a full circle may advantageously facilitate access of a patient to the image acquisition region of the magnetic resonance system.

In a further embodiment of the magnetic resonance imaging system, the magnetic field generator comprises a first magnet and a second magnet, wherein the first magnet is configured to generate a first magnetic field inside the image acquisition region and the second magnet is configured to generate a second magnetic field inside the image acquisition region. The second magnet may be carried by a second magnet holder. In an exemplary embodiment, a relative position of the second magnet holder and the first magnet holder is constant. In one embodiment, the first magnet holder and the second magnet holder are mounted on a first carrier element of the mechanical guiding rail. However, the second magnet holder may also be mounted on a second carrier element of the mechanical guiding rail. It is conceivable, that the second carrier element comprises a spacing element which is connected to the first carrier element in order to ensure a constant distance between the first carrier element and the second carrier element. The first magnetic field may comprise a first imaging volume and the second magnetic field may comprise a second imaging volume. In one embodiment, the first imaging volume may be spatially separated from the second imaging volume in such a way, that any intersection or overlap between the first imaging volume and the second imaging is avoided. In providing a first imaging volume and a second imaging volume, a total imaging volume of the magnetic resonance system may be increased. Thus, a time interval required to acquire magnetic resonance signals from a diagnostically relevant region can be advantageously reduced. It is also conceivable, that the magnetic field generator comprises a third magnet, a fourth magnet or a plurality of further magnets, which are configured in a similar way.

In a further embodiment, a subset of the first imaging volume overlaps with a subset of the second imaging volume. It is also conceivable, that the first imaging volume corresponds to the second imaging volume. In this case, the second magnet may favorably be used to adjust and/or improve a magnetic field strength, a magnetic field homogeneity and/or a magnetic field gradient in the first imaging region provided by the first magnet. However, by using at least two magnets that share an imaging volume, more sophisticated imaging protocols, such as an application of pre-polarizing magnetic field pulses, can be applied.

In one embodiment of the magnetic resonance imaging system, the rotation system is configured to move the first magnet from a first end position on the rotation trajectory to a predefined position on the rotation trajectory and move the second magnet from the predefined position to a second end position on the rotation trajectory. It is conceivable, that a relative position of the first magnet and the second magnet is constant. In an exemplary embodiment, the first magnet and the second magnet are mounted on the rotation system in such a way, that an angle between a first vector directing from a center of the first magnet to the rotation center and a second vector directing from a center of the second magnet to the rotation center is constant. Moving the first magnet and the second magnet along the rotation trajectory by an amount which corresponds to the constant angle between the first vector and the second vector may result in positioning the first magnet from a first end position to the predefined position, while the second magnet is moved from the predefined position to the second end position. In providing a rotation system with a first end position and a second end position, a reproducibility of positioning of the first magnet and the second magnet on the rotation trajectory can be enhanced advantageously. Furthermore, by moving the first imaging volume of the first magnet and the second imaging volume of the second magnet in a constant relative position along a rotation trajectory, a diagnostically relevant volume may be covered in a time-efficient manner.

In a further embodiment of the magnetic resonance imaging system, the magnetic field generator comprises at least one active shim coil which is configured to reduce undesirable interactions of the first magnetic field and the second magnetic field. In an exemplary embodiment, the at least one active shim coil comprises at least one electrical conductor which may be mounted on a magnet holder and/or a magnet of the magnetic field generator. The at least one active shim coil may comprise an electrical connection to a power supply configured to pass a current through the at least one electrical conductor. The at least one active shim coil may be designed in such a way, that passing a current through the at least one electrical conductor generates a shimming magnetic field. This shimming magnetic field may be superimposed on at least a part of the first magnetic field and/or at least a part of the second magnetic field. It is conceivable, that the shimming magnetic field confines the first magnetic field and/or the second magnetic field in order to reduce undesirable interactions between the first magnetic field and the second magnetic field. However, the shimming magnetic field may also be configured to enhance the homogeneity of the first magnetic field and/or the second magnetic field. In providing at least one active shim coil, interactions between the first magnetic field and the second magnetic field may favorably be reduced. Furthermore, an effect of the at least one active shim coils on the first magnetic field and/or the second magnetic field may favorably be adjusted via the current passing through the at least one electrical conductor.

In a further embodiment, the magnetic field generator comprises at least one shim iron which is configured to reduce undesirable interactions of the first magnetic field and the second magnetic field. The at least one shim iron may be positioned and/or shaped in such a way to efficiently reduce interactions between the first magnetic field and the second magnetic field. It is also conceivable, that the at least one shim iron further acts as a magnetic pole, which may adjust a direction and/or the homogeneity of the first magnetic field and/or the second magnetic field. In providing at least one passive shim iron, costs and/or spatial requirements for power supply can advantageously be avoided.

In a further embodiment of the magnetic resonance imaging system, the magnetic field generator includes a magnetic field gradient system comprising at least one gradient coil, wherein the at least one gradient coil is configured to provide a magnetic gradient field in the image acquisition region. The at least one gradient coil may comprise an electrical conductor arranged in such a way, that a magnetic gradient field is provided in the image acquisition region, when an electric current is passed through the electrical conductor. The electrical conductor may comprise a single wire or a plurality of wires which consist of a material with high electrical conductivity. For example, a wire of the electrical conductor may consist of gold, silver, copper or aluminum. It is also conceivable, that the electrical conductor is coated or galvanized with a material with high electrical conductivity. The electrical conductor may be arranged in a complex, two-dimensional or three-dimensional shape. It is conceivable, that the electrical conductor of the at least one gradient coil is connected to a power supply configured to pass an electric current through the electrical conductor. The at least one gradient coil may further be connected to a cooling system, e.g. a fluid cooling system, configured to cool the electrical conductor. In an exemplary embodiment, the at least one gradient coil is configured to generate a magnetic gradient field in an imaging volume, such as the first imaging volume and/or the second imaging volume. The magnetic gradient field may be superimposed on a magnetic field, such as the first magnetic field and/or the second magnetic field, in order to provide a predetermined gradient in magnetic field strength. This gradient in magnetic field strength may represent a spatial encoding gradient used for spatial encoding of magnetic resonance signals acquired from the imaging volume. However, the magnetic gradient field of the least one gradient coil may also be configured to manipulate a phase or a frequency of nuclear spins in the imaging volume. Thus, the magnetic gradient field of the least one gradient coil may also represent a phase encoding gradient or a frequency encoding gradient. In providing the at least on gradient coil, magnetic resonance signals may favorably be assigned to a place of origin within the image acquisition region of the magnetic resonance system.

In one embodiment of the magnetic resonance imaging system, the at least one gradient coil is carried by the magnet holder. The at least one gradient may be reversibly mounted on the magnet holder via any kind of locking and/or frictional connection. For example, a connection between the at least one gradient coil and the magnet holder may be provided via a suitable fastener mechanically joining the magnet holder with the at least one gradient coil. It is also conceivable, that the at least one gradient coil is mounted on a supporting structure, as for example a panel or a contoured panel, which may in turn be mounted on the magnet holder. However, the at least one gradient coil may also be materially bonded to the supporting structure and/or the magnet holder, for example via a suitable adhesive. In an exemplary embodiment, a relative position of the at least one magnet and the at least one gradient coil is constant, while the at least one magnet is positioned along the rotation trajectory. In mounting the at least one gradient coil on the magnet holder of the magnetic field generator, the at least one gradient coil may be positioned in close proximity to the imaging volume provided by the at least one magnet. Thus, a required dimension of the magnetic gradient field provided by the at least one gradient coil can be reduced or matched with the imaging volume. Thus, costs and/or and spatial requirements associated with the at least one gradient coil can favorably be reduced.

In a further embodiment of the magnetic resonance imaging system, the rotation system comprises a gradient coil holder configured to carry the at least one gradient coil, wherein the mechanical guiding rail is configured to guide the gradient coil holder along the rotation trajectory. The mechanical guiding rail may be configured as described above. By using the mechanical guiding rail, the magnet holder, the at least one gradient coil and the at least one magnet may favorably be positioned along the rotation trajectory by using a single carrier element. Thus, spatial requirements for multiple carrier elements and dedicated motors may advantageously be avoided. It is also conceivable, that the magnet holder, the at least one gradient coil and the at least one magnet are carried by a plurality of carrier elements connected via spacing elements as described above. By using the mechanical guiding rail to guide the gradient coil holder along the rotation trajectory, an accuracy of positioning the at least one gradient coil may favorably be enhanced.

In one embodiment of the magnetic resonance imaging system, the magnetic gradient field generated by the at least one magnet is oriented at an angle of at least 50°, of at least 70° or at an angle of 90° to the magnetic gradient field generated by the at least one gradient coil. It is conceivable, that the magnetic gradient field generated by the at least one gradient coil is superimposed on the magnetic gradient field generated by the at least one magnet in the imaging volume of the at least one magnet. Thus, a three-dimensional magnetic gradient field may be provided in the imaging volume, which may be used for spatial encoding of magnetic resonance signals in the imaging volume. In an exemplary embodiment, in order to facilitate spatial encoding of the magnetic resonance signals, the magnetic gradient field generated by the at least one gradient coil and the magnetic gradient field generated by the at least one magnet are arranged at an angle of 90°. However, in order to reduce spatial requirements and/or a complexity of a constructive design of the magnetic resonance imaging system, the at least one magnet and the at least one gradient coil may also be arranged in such a way, that the angle between the magnetic gradient fields of the at least one gradient coil and the at least one magnet deviates from a 90° angle. For example, the angle between the magnetic gradient field provided by the at least one magnet and the magnetic gradient field provided by the at least one gradient coil may be lower than 90° or higher than 90°. By orienting the magnetic gradient field provided by the at least one magnet and the magnetic gradient field provided by the at least one gradient coil at an angle, an accuracy of spatial encoding of magnetic resonance signals acquired from the imaging region may be increased advantageously. Particularly, by using an angle of 90°, a Cartesian coordinate system may favorably be used as a basis for spatial encoding as well as image reconstruction.

In one embodiment of the inventive magnetic resonance imaging system, the processor is configured to perform spatial encoding of magnetic resonance signals acquired from the image acquisition region in dependence of a change of the magnetic field induced by the positioning of the at least one magnet along the rotation trajectory and the magnetic gradient field of the at least one gradient coil. As described above, the at least one magnet may be moved along the rotation trajectory, whereby the magnetic field generated by the at least one magnet is moved accordingly within the image acquisition region. In order to excite nuclear spins with a predefined Larmor frequency, a radiofrequency excitation pulse with a frequency corresponding to the Larmor frequency may be emitted into the image acquisition region via the at least one radiofrequency antenna. The magnetic resonance signals of the excited nuclear spins may also be acquired by the at least one radiofrequency antenna and assigned to specific positions within the image acquisition region based on known characteristics of the magnetic gradient field provided by the at least one magnet and the at least one gradient coil. For example, when moving the at least one magnet along the rotation trajectory, nuclear spins within the imaging volume of the at least one magnet are aligned along the magnetic field provided by the at least one magnet. The nuclear spins within the imaging volume may be excited by a radiofrequency excitation pulse, whereas nuclear spins outside the imaging volume are excited to a lesser degree or remain unexcited.

Magnetic resonance signals of the excited nuclear spins may be assigned to specific positions within the image acquisition region in dependence of the known position of the at least one magnet along the rotation trajectory and the known characteristic of the magnetic gradient field provided by the at least one magnet and the at least one gradient coil. Thus, a motion of the at least one magnet along the rotation trajectory may be used for spatial encoding of the magnetic resonance signals acquired from the imaging volume. By spatially encoding magnetic resonance signals in the image acquisition region in dependence of a change of the magnetic field induced via positioning of the at least one magnet along the rotation trajectory, a use of further gradient coils, as for example a second gradient coil and/or a third gradient coil, may be avoided. Thus, costs and/or spatial requirements of the magnetic resonance imaging system may advantageously be reduced.

In a further embodiment of the magnetic resonance imaging system, the magnetic field gradient system comprises a first gradient coil configured to generate a first magnetic gradient field in the image acquisition region and a second gradient coil configured to generate a second magnetic gradient field in the image acquisition region. The first gradient coil may be configured to provide a phase encoding gradient, whereas the second gradient coil may be configured to provide a frequency encoding gradient. A spatial encoding gradient may be provided by the at least one magnet as described above. For this purpose, a magnetic gradient field generated by the at least one magnet may be oriented at an angle of at least 50°, at least 70° or at an angle of 90° to a first magnetic gradient field provided by the first gradient coil and/or a second magnetic gradient field provided by the second gradient coil.

In one embodiment, the first gradient coil may be configured to generate a first magnetic gradient field oriented azimuthally to a dental arch of a patient, whereas the second gradient coil may be configured to generate a second magnetic gradient field oriented along a cranio-caudal direction of the patient. The first gradient coil and the second gradient coil may be moved along the rotation trajectory of the rotation system. However, it is also conceivable, that a position of the second gradient coil is fixed, whereas the first gradient coil may be moved along the rotation trajectory. In providing the first gradient coil, the second gradient coil and the at least one magnet, spatial encoding of magnetic resonance signals acquired from the image acquisition region may be performed with a minimum of components. Thus, costs and/or spatial requirements of the magnetic resonance imaging system can be reduced advantageously.

In a further embodiment, the magnetic field gradient system comprises a third gradient coil configured to generate a third magnetic gradient field in the image acquisition region. The third magnetic gradient field may represent a spatial encoding gradient used for spatial encoding of the magnetic resonance signals acquired from the image acquisition region. In this embodiment, the at least one magnet is configured to provide an approximately homogenous magnetic field within the image acquisition region. In providing a third gradient coil, the at least one magnet may be optimized to provide a homogenous magnetic field in order to enhance a quality of magnetic resonance imaging data.

In one embodiment of the magnetic resonance imaging system, the magnetic field gradient system comprises two Maxwell coils which are aligned to each other in an angular fashion. It is conceivable, that the two Maxwell coils are fed with equally directed currents to provide a magnetic gradient field. A distance between the two coils may amount to $\sqrt{3}\cdot R$, wherein R represents a radius of a Maxwell coil. In an exemplary embodiment, the radius R is the same for both Maxwell coils. A Maxwell coil arrangement may provide a magnetic gradient field with very linear gradient characteristics. Thus, an accuracy of spatial encoding of magnetic resonance signals in the imaging region can advantageously be increased.

In an exemplary embodiment of the magnetic resonance imaging system, a contour of the rotation trajectory corresponds to a contour of a body region of a patient and the rotation system is configured to position the magnet holder along the contour of the body region of the patient. A contour of a body region of the patient may be at least a segment of a circumference of an axial cross-section of the body or body part of the patient. For example, the contour of a breast of the patient may comprise a segment of an outline of an axial cross-section of the breast region of the patient. In a similar fashion, the contour of the rotation trajectory may correspond to an outline of an abdomen of the patient or an outline of a head of the patient. However, it is also conceivable, that the contour of the rotation trajectory corresponds to the contour of an arm, a leg or another extremity of the patient. The rotation system may comprise a rigid rotation trajectory, which may be configured to approximate a contour of a targeted body region of the patient while also taking into account a statistic size distribution of a targeted group of patients. However, the rotation system may also comprise flexible elements, such as hinges or movable joints, which may be adapted to accommodate different body sizes and/or different body regions. Thus, the magnetic resonance system may be configured to perform cardiac imaging of a heart, mammography imaging of a breast, neurological imaging of a brain, urological imaging of a prostate, orthopedic imaging of a joint, ophthalmological imaging of an eye and/or dental imaging of a jaw region of the patient. By matching the contour of the rotation trajectory with the contour of a body region of the patient, a distance between the magnet holder and a surface of the body of the patient can be reduced when moving the magnet holder along the contour of the body region of the patient. Thus, costs and/or spatial requirements associated with providing a magnetic field and/or a magnetic gradient field configured to operate at higher distances to the patient can advantageously be reduced.

In one embodiment of the magnetic resonance imaging system, the contour of the rotation trajectory corresponds to a contour of a jaw region of the patient and the magnetic resonance imaging system is configured to acquire magnetic resonance signals of a tooth and/or a jaw of the patient. As described above, the contour of the rotation trajectory may be matched with at least a segment of an outline of an axial cross-section of the jaw region of the patient. Thus, the imaging volume may be moved along at least a part of a dental arch of the patient when moving the at least one magnet along the rotation trajectory. In one embodiment, the rotation trajectory may be configured to match a typical curvature of a dental arch of a targeted group of patients. Thus, magnetic resonance signals of a tooth and/or a plurality of teeth of the patient may be acquired. In providing a dedicated magnetic resonance system for imaging of the jaw region of the patient, an application of ionizing radiation commonly associated with current imaging modalities for diagnostic imaging of the jaw region, can favorably be avoided.

According to one embodiment of the magnetic resonance imaging system, the magnetic field generator comprises an adjustment mechanism configured to adjust a position and/or a shape and/or an orientation of the rotation system in order to accommodate for a geometry of the body region of the patient. The adjustment mechanism may comprise a hinge, a moveable joint and/or a flexible element configured to adjust a curvature, an angle and/or a shape of the rotation trajectory. For example, the rotation system may comprise one or more hinges configured to match a curvature of the arc-shaped element with a contour of the jaw region of the patient. In another example, the mechanical guiding rail may comprise a flexible material such as an elastomer, a viscoelastic polymer, a synthetic or natural rubber, or the like. Thus, the mechanic guiding rail may be bent or shaped by the adjustment mechanism of the magnetic field generator in order to match the geometry of the body region of the patient. In providing an adjustment mechanism, a contour of the rotation trajectory may favorably be adjusted to accommodate differently shaped body regions of individual patients. Thus, a mean spacing between the at least one magnet and the surface of a diagnostically relevant region of differently sized patients can be reduced. By ensuring a low spacing between the at least one magnet and the surface of the patient, a signal-to-noise ratio of the magnetic resonance imaging system can be increased advantageously.

In one embodiment of the magnetic resonance imaging system, a dimension of an imaging volume provided by the at least one magnet is lesser than 8 cm in a lateral direction, lesser than 5 cm in a ventrodorsal direction and lesser than 5 cm in a craniocaudal direction. An imaging volume with these dimensions may encompass, for example, a tooth, several teeth, a dental arch, an eye, a segment of the brain, a segment of the heart or parts of other organs of the patient. As described above, the imaging volume may be moved within the image acquisition region in conjunction with the at least one magnet in order to acquire magnetic resonance signals from a diagnostically relevant volume (imaging region) of the examination object. In providing an imaging volume according to the dimensions given above, costs and/or spatial requirements of the magnetic field generator can advantageously be reduced in comparison to conventional magnetic resonance imaging systems.

According to a further embodiment of the magnetic resonance imaging system, the magnetic field generator further comprises a distance adapter configured to adjust a spacing between the magnet holder and a surface of the patient. The distance adapter may be configured to position the magnet holder and/or the at least one magnet along the radial direction of the rotation trajectory. For example, the distance adapter may move the magnet holder and/or the at least one magnet along the radial direction towards the rotation center of the rotation system. The distance adapter may comprise a rail system and/or a telescope system configured to extend and retract the at least one magnet and/or the magnet holder along said radial direction. In an exemplary embodiment, the distance adapter comprises a motor which is configured to move the magnet holder and/or the at least one magnet along the radial direction either automatically or in dependence of a signal generated via a remote control operated by an operator of the magnetic resonance imaging system. In providing a distance adapter, the at least one magnet may favorably be guided along a complex body contour of the patient without having to shape the rotation trajectory accordingly. Furthermore, costs and/or spatial requirements for a magnet with higher magnetic field strengths and/or higher magnetic field homogeneity positioned in greater distance to the surface of the examination object can be avoided.

In a further embodiment of the magnetic resonance imaging system, the distance adapter comprises a sensor configured to determine a distance between the magnet holder and the surface of the patient, wherein the distance adapter is configured to adjust a spacing between the magnet holder and the surface of the patient in dependence of the distance value. The sensor may comprise any measurement principle suitable for determining the distance value between the magnet holder and the surface of the patient. For example, the sensor may comprise a spring mechanism which is in contact with the surface of the patient. The sensor may be configured to determine a mechanical force exerted on the surface of the patient via the spring mechanism. The sensor may also be configured to determine the distance value in dependence of the mechanical force. However, the mechanical force may also be transmitted to the processor of the magnetic resonance imaging system via a suitable signal connection. In this instance, the processor may be configured to determine the distance value in dependence of the mechanical force. It is also conceivable, that the spring mechanism is in contact with a mask or a protective cover positioned on the surface of the patient in order to protect the patient from possible injuries.

In an exemplary embodiment, the sensor may comprise a contact-free measurement principle. A contact-free measurement principle may comprise any measurement technology suitable for determining the distance value while avoiding a mechanical contact with the surface of the patient. For instance, the sensor may be an optical sensor configured to determine the distance value in dependence of an electromagnetic wave, such as a light wave, a radar wave or an ultrasound wave, reflected from the surface of the patient. For this purpose, the sensor may be configured to irradiate electromagnetic waves in a direction of the patient and receive electromagnetic waves reflected from the surface of the patient. In one example, the distance value may be determined in dependence of a time interval between an emission of the electromagnetic wave and a reception of the reflected electromagnetic wave.

The distance adapter may be configured to adjust a spacing between the magnet holder and the surface of the patient in dependence of the distance value. The distance adapter may comprise an input interface configured to receive the distance value or the mechanical force from the sensor or the processor via a suitable corded or wireless signal connection. It is also conceivable, that the distance adapter comprises a processor configured to determine a suitable spacing between the magnet holder and the surface of the patient in dependence of the distance value or the mechanical force determined via the sensor. Furthermore, the spacing between the magnet holder and the surface of the surface of the patient may also be determined via a processor or a controller of the magnetic resonance imaging system. The processor or the controller may be configured to output a control signal to the distance adapter in order to adjust the spacing between the magnet holder and the surface of the jaw region. A motor of the distance adapter may be configured to move the magnet holder along a radial direction of the rotation trajectory in dependence of the control signal provided by the processor or the controller. In providing a sensor configured to determine the distance value between the magnet holder and the surface of the patient, a position of the at least one magnet can be adjusted to account for an individual contour of body region of the patient. Thus, the at least one magnet can favorably be guided along complex contours, such as a facial region or a jaw region, in close proximity to the surface of the patient.

In one embodiment of the magnetic resonance imaging system, the radiofrequency system is configured to acquire magnetic resonance navigator data from the image acquisition region, wherein the processor is configured to determine a distance value between the magnet holder and the surface of the patient in dependence of the magnetic resonance navigator data and wherein the distance adapter is configured to adjust a spacing between the magnet holder and the surface of the patient in dependence of the distance value. The magnetic resonance navigator data may comprise regularly or sparsely sampled magnetic resonance signals from the imaging volume. It is also conceivable, that the magnetic resonance signals are acquired with a low spatial resolution. The magnetic resonance navigator data may be transferred to the processor of the magnetic resonance system in order to identify anatomical structures covered by the magnetic resonance navigator data. For this purpose, the processor may be configured to reconstruct navigator images in dependence of the magnetic resonance navigator data (e.g. via Fourier transformation). The processor may comprise an image processor configured to identify anatomical structures in the navigator images in dependence of contrasts and/or signal intensities of picture elements (pixels) or volume elements (voxels) of the navigator images. In dependence of the identified anatomical structures, as well as a known characteristic of the magnetic field used to acquire the navigator data (e.g. a known distance between the imaging volume and the at least one magnet), the processor may determine the distance value between the magnet holder and the surface of the patient. An anatomical structure may comprise at least a part of a tooth, a tooth, several teeth, a part of a jawbone, a jawbone or the like. However, anatomical structures of other body regions may also be used to determine the distance value between the magnet holder and the surface of the patient in a similar fashion. By using magnetic resonance navigator data to determine the distance value between the magnet holder and the surface of the jaw region of the patient, costs and/or spatial requirements associated with a sensor may advantageously be avoided. Furthermore, undesirable interference between the sensor and the magnetic field of the at least one magnet may favorably be avoided.

In one embodiment of the magnetic resonance imaging system, the first magnet is configured to generate a pulsed first magnetic field and the second magnet is configured to generate a homogenous second magnetic field and wherein the magnetic resonance imaging system comprises a controller configured to:

control the first magnet to generate the pulsed first magnetic field in order to pre-polarize nuclear spins inside an imaging volume and switch off the first magnet when the second magnet is switched on and control the second magnet to generate the homogeneous second magnetic field inside the imaging volume during a radiofrequency excitation of the pre-polarized spins and during an acquisition of magnetic resonance signals from the imaging volume.

The imaging volume may correspond to the second imaging volume provided by the second magnet. Thus, the first magnet may be controlled to pre-polarize nuclear spins within a known volume which becomes the imaging volume when the second magnet is switched on and the first magnet is switched off.

In an exemplary embodiment, the magnetic field strength of the pulsed first magnetic field ranges between 0.3 to 1.5 Tesla, and more specifically between 0.5 to 1.0 Tesla. The magnetic field strength of the second magnetic field may be lower than the magnetic field strength of the pulsed first magnetic field. For example, the magnetic field strength of the second magnetic field may comprise several Milli-Tesla, several ten Milli-Tesla, several hundred Milli-Tesla or more. In an exemplary embodiment, the magnetic field strength of the second magnetic field ranges between 0.05 Tesla and 0.5 Tesla.

The first magnet may be an electromagnet configured to provide a pulsed first magnetic field when an electric current is passed through an electric conductor of the first magnet. The pulsed first magnetic field may be homogeneous or inhomogeneous. Particularly, the pulsed first magnetic field generates a pre-polarization of nuclear spins within the imaging volume.

The first magnet may be ramped down, when the second magnet is ramped up. For example, the electric current passing through the first magnet may be stopped when electric current is passed through the second magnet. A time interval, wherein electric current is passed through the first magnet may overlap with a time interval, wherein electric current is passed through the second magnet. However, after ramping down the first magnet there might also be a short time interval, wherein no current is passed through the first magnet and the second magnet. The pulsed first magnetic field is turned on or off in dependence of a control signal provided by the controller of the magnetic resonance imaging system. In an exemplary embodiment, the control signal is synchronized with an imaging sequence of a magnetic resonance imaging examination. For example, the control signal may be synchronized with a repetition time of the imaging sequence which may range between 2 Milliseconds 3000 Milliseconds.

The second magnet may comprise an electromagnet, a permanent magnet or a superconducting magnet. The second magnetic field may be oriented along a left-right direction of the patient, an anterior-posterior direction of the patient or any direction in between. The second magnet may confine the image acquisition region in at least in one direction, thus providing an asymmetric magnet arrangement. However, it is also conceivable, that the second magnet encompasses the image acquisition region along a circumferential direction, thus providing a symmetric magnet arrangement. In the latter case, the first magnet may be moved along the rotation trajectory in order to pre-polarize nuclear spins in an imaging region, while the second magnet remains in a stationary position. As described above, the first magnet may be moved continuously or in a step-by-step fashion, whereby magnetic resonance signals of an imaging volume may be acquired in each step. In an exemplary embodiment, the homogeneity of the second magnetic field is higher than the homogeneity of the pulsed first magnetic field. For example, a deviation between the highest magnetic field strength and the lowest magnetic field strength (peak-to-peak ratio) of the pulsed first magnetic field may amount to about 20%. In comparison, a peak-to-peak ratio of the second magnetic field may be less than 0.1%.

In one embodiment, the first magnet and the second magnet may be arranged in a Helmholtz configuration or a Helmholtz-like configuration. It is conceivable, that a relative position of the first magnet and the second magnet is constant when the first magnet and the second magnet are moved along the rotation trajectory. For example, maintaining a constant relative position of the first magnet and the second magnet may comprise maintaining a distance between the first magnet and the second magnet along the rotation trajectory. By moving the first magnet and the second magnet along the rotation trajectory, an orientation of the first magnet and the second magnet in a direction of the image acquisition region can favorably be ensured.

In one embodiment, the magnetic field generator comprises a third magnet, a fourth magnet or a plurality of magnets. Thus, the magnetic resonance imaging system may be configured to provide a plurality of pulsed magnetic fields pre-polarizing nuclear spins within a plurality of separate or disjoint imaging volumes. For this purpose, the second magnetic field of the second magnet may favorably encompass the plurality of imaging volumes of the pulsed magnetic fields. In providing a plurality of pulsed magnetic fields, a time period required for magnetic resonance imaging of an imaging region can advantageously be reduced. It is also conceivable to exploit a (partly) inhomogeneous nature of the magnetic field drop when switching-off the first magnet for spatial encoding of magnetic resonance signals. Thus, a number of gradient coils for spatial encoding can be reduced as well as costs and/or spatial requirements for gradient power amplifiers and power supply.

In a further embodiment, a gradient power amplifier may be configured to alternatingly supply power to a gradient coil and the first magnet in such a way, that power is supplied to the gradient coil when the first magnet is ramped down. Thus, costs and/or spatial requirements for power supply and power amplifiers may favorably be reduced.

Metal orthopedic hardware and/or dental prosthesis may cause significant magnetic field distortion when imaging at high magnetic field strengths. In providing a pre-polarization of nuclear spins within the imaging volume and acquiring magnetic resonance signals when applying the second magnetic field with a lower magnetic field strength, susceptibility artifacts in magnetic resonance images may favorably be reduced.

FIG. 1 holds a schematic representation of an inventive magnetic resonance imaging system 10 configured to perform a magnetic resonance imaging examination of a jaw region of a patient 15. The application of the magnetic resonance imaging system 10 for imaging of the jaw region of the patient 15 is to be regarded as an example. The inventive magnetic resonance imaging system 10 may also be configured to perform cardiac imaging, mammography imaging, neurological imaging, urological imaging, orthopedics imaging, ophthalmologic imaging, prostate imaging or imaging of other body regions of the patient. For this purpose, the magnetic field generator 13 and/or the rotation system 30 of the magnetic resonance imaging system 10 may be positioned in proximity to a diagnostically relevant body region of the patient 15. In particular, the magnetic field generator 13 and/or the rotation system 30 may be configured to match the diagnostically relevant body region of the patient 15 in such a way, that a contour of the rotation trajectory 32 (see FIG. 3) matches a contour of the diagnostically relevant body region of the patient 15.

The magnetic resonance imaging system 10 comprises a magnetic field generator 13 and an image acquisition region 14 configured to receive an examination object 15, in particular a jaw region of the patient 15. The image acquisition region 14 is at least partially enclosed by a rotation system 30 (see FIG. 9) of the magnetic field generator 13. The patient 15 may access the image acquisition region 14 by means of a patient positioning device 16. However, the magnetic field generator 13 may comprise a support system 11 including an adjustment mechanism 12 for adjusting a position and/or an orientation of the magnetic field generator 13 with respect to the patient 15. For example, the adjustment mechanism 12 may comprise a swivel joint configured to rotate the magnetic field generator 13 along a rotation direction Wx and a rotation direction Wy. A position of the magnetic field generator 13 along a Y-direction and a Z-direction may be adjusted via a suitable telescope system and/or rail system integrated within the support system 11. Of course, other embodiments of the support system 11 and the adjustment mechanism 12 are conceivable.

The magnetic field generator 13 comprises at least one magnet 17 (see FIG. 3) which is configured to generate a magnetic field in the image acquisition region 14. The magnetic field generator 13 may further comprise a magnetic field gradient system 60 for generating magnetic gradient fields used for spatial encoding of magnetic resonance signals acquired during a magnetic resonance imaging examination. Additionally, the magnetic field generator 13 comprises a radiofrequency antenna (not shown) configured to emit a radiofrequency excitation pulse in the image acquisition region 14. The radiofrequency antenna may also be configured to receive magnetic resonance signals from the image acquisition region 14.

In order to control the magnetic field generator 13 as well as the radiofrequency antenna, the magnetic resonance imaging device 10 comprises a controller 20. The controller 20 is configured to control the magnetic resonance imaging system 10 to perform an imaging sequence. For this purpose, the controller 20 may comprise a signal connection with a gradient controller 22 and a radiofrequency antenna controller 21. It is also conceivable, that the gradient controller 22 and the radiofrequency antenna controller 21 are integrated in the controller 20. Furthermore, the controller 20 may comprise a processor 24 configured to coordinate an acquisition and/or an evaluation of magnetic resonance signals acquired from the image acquisition region 14. It is conceivable, that the processor 24 is also configured to evaluate data such as magnetic resonance signals and/or magnetic resonance image data. The controller 20 may comprise a controller, a microcontroller, an analog circuit, a logic unit and the like. The processor 24 may comprise a processor, such as a CPU, a GPU and the like. It is also conceivable, that the controller 20 and/or the processor 24 comprise a memory and/or an internal storage, such as a RAM, a ROM, a PROM, an EPROM, an EEPROM, a flash memory, as well as an HDD, an SSD and the like. In an exemplary embodiment, the controller 20 includes processor circuitry that is configured to perform one or more functions and/or operations of the controller 20, including controlling the magnetic resonance imaging system 10 to perform an imaging sequence.

Control information, such as imaging parameters and/or reconstructed image data, can be displayed on a display unit 25. The display unit 25 may comprise at least one monitor configured to display control information and/or image data of the magnetic resonance imaging system 10 to an operator of the magnetic resonance imaging system 10. The magnetic resonance imaging system 10 may further comprise an input unit 26 configured to receive information and/or parameters input by the operator during a magnetic resonance imaging examination.

The illustrated magnetic resonance imaging system 10 may of course include further components that magnetic resonance imaging systems 10 usually comprise. The general mode of operation of a magnetic resonance imaging system 10 is well-known to the person skilled in the art, so a further description of the general components or a sequencing of a magnetic resonance imaging examination is not deemed necessary.

FIG. 2 shows a schematic representation of a housing 27 of the magnetic resonance imaging system 10 according to the disclosure. The housing 27 may be configured to shield the image acquisition region from electromagnetic interference and/or radiofrequency interference. In one embodiment, the housing 27 comprises an electrically conducting element (not shown) configured to divert electromagnetic and/or radiofrequency interference, thus protecting the image acquisition region from external interfering signals. The housing 27 may further comprise noise absorbing materials, such as rubber or foam, in order to reduce noise from the magnetic field generator 13 and/or the magnetic gradient field system 60.

The housing 27 may comprise a hinge 36 or moveable joint configured to guide a rotation of the housing 27 along the Wx-direction. In the depicted embodiment, the housing 27 is placed over a head of the patient 15 positioned within the image acquisition region 14 of the magnetic field generator 13. The housing 27 may comprise a gap or a recess for accommodating the magnetic field generator 13, when the housing 27 is positioned over the head of the patient 15. The housing 27 comprises an opening, such as a circular hole or an oval hole in order to accommodate the head of the patient 15 within the housing 27. It is conceivable, that the magnetic field generator 13 is mechanically attached to the housing 27. However, the housing 27 and the magnetic field generator 13 may also be separate components as indicated in FIG. 2.

FIG. 3 depicts a schematic representation of the magnetic field generator 13 of a magnetic resonance imaging system 10 according to the disclosure. The depiction comprises a cross-section of a dental arch 41 of the patient 15 positioned within the image acquisition region 14. The magnetic field generator 13 comprises a magnet 17 which is positioned along a rotation trajectory 32 encompassing the dental arch 41 of the patient 15 along an outer perimeter. The magnetic field generator 13 comprises a rotation center 31 which may represent, for example, the center of the rotation trajectory 32 or the center of a circle circumscribing the rotation trajectory 32. The line 34 indicates an orientation of a vector directing from an arbitrarily chosen spot on the surface of the magnet 17 to the rotation center 31 along a radial direction of the rotation trajectory 32.

The magnet 17 generates a magnetic field within the image acquisition region 14. The magnetic field comprises an imaging volume 19 covering a tooth 42 of the dental arch 41. By moving the magnet 17 along the rotation trajectory 32 during a magnetic resonance imaging examination, the imaging volume 19 is guided along the dental arch 41 of the patient 15, thus covering a plurality of teeth or all of the teeth of the patient 15. A width, a length and a height of the imaging volume 19 may be matched with a width, a length and a height of a tooth 42 or a plurality of teeth of a patient 15. The imaging region 18 represents a volume from which magnetic resonance signals may be acquired when the imaging volume 19 is moved along the dental arch 41. In an exemplary embodiment, the dimension of the imaging region 18 is lesser than 8 cm in a lateral direction, lesser than 5 cm in a ventrodorsal direction and lesser than 5 cm in a craniocaudal direction.

The magnetic field generator 13 may comprise a sensor 51 configured to determine a distance value between a magnet holder 33 and/or the magnet 17 and a surface 43 of the jaw region of the patient 15. In an exemplary embodiment, the sensor 51 is an optical sensor configured to emit an infrared light pulse in the direction of the patient 15 and receive the reflected infrared light pulse in order to determine the distance value. The sensor 51 may transmit the distance value as an analog or digital signal to the processor 24 via a suitable signal connection 23a. In an exemplary embodiment, the processor 24 is configured to process the distance value and control a distance adapter 35 to adjust a spacing between the surface 43 of the jaw region of the patient 15 via the signal connection 23b. Thus, the magnet 17 may be moved to a desired position along the radial direction indicated by line 34. In the depicted example, the magnet 17, the distance adapter 35 and the sensor 51 are carried by the magnet holder 33. However, the magnet 17, the distance adapter 35 and the sensor 51 may be arranged in any other feasible configuration.

In order to account for an oval outline of the dental arch 41, the distance between the rotation center 31 and the magnet 17 may be adjusted via the distance adapter 35. However, it is also conceivable, that the rotation center 31 is moved in an anterior-posterior direction of the patient 15, while the magnet 17 is moved along an approximately circular rotation trajectory 32.

For example, the movement of the rotation center 31 may be provided via the support system 11 and/or the adjustment mechanism 12. In still a further embodiment, the rotation trajectory 32 comprises an oval shape, approximately matching the oval outline of the dental arch 41 of the patient 15.

FIG. 4 shows a schematic representation of an imaging region 18 of the magnetic resonance imaging system 10 according to the disclosure. As depicted in FIG. 3, a height of the imaging volume 19 may be chosen in such a way, that a tooth of an upper dental arch 41a and a lower dental arch 41b are encompassed by the imaging volume 19. Thus, when moving the magnet 17 along the rotation trajectory 32, magnetic resonance signals may be acquired from the imaging region 18 covering both dental arches 41a and 41b of the patient 15. However, if a magnetic field homogeneity in the cranio-caudal direction of the patient 15 is insufficient, the magnetic resonance imaging examination of the jaw region of the patient 15 may also be divided into a first examination covering the upper dental arch 41a and a second examination covering the lower dental arch 41b. In an exemplary embodiment, this may be accomplished by either moving the magnetic field generator 13 along the Y-direction via the support system 11 or by moving the patient 15 via the patient positioning device 16 (see FIG. 1).

FIG. 5 shows a schematic representation of another embodiment of the magnetic field generator 13. In this embodiment, the magnetic field generator 13 comprises a first magnet 17a and a second magnet 17b arranged in a predefined relative position along the rotation trajectory 32. The first magnet 17a generates a first imaging volume 19a and the second magnet 17b generates a second imaging volume 19b within the image acquisition region 14. When starting a magnetic resonance imaging examination, the first magnet 17a may positioned at the first end position 37 on the rotation trajectory 32, whereas the second magnet 17b may be positioned at a predefined position 39 on the rotation trajectory 32. During the magnetic resonance imaging examination, the first magnet 17a is moved along the rotation trajectory 32 from the first end position 37 to the predefined position 39, while the second magnet 17b is moved from the predefined position 39 to the second end position 38. Thus, an imaging region 18 covering the dental arch 41 of the patient 15 may be subdivided into an imaging region 18a covered by the first magnet 17a and an imaging region 18b covered by the second magnet 17b.

In an exemplary embodiment, an angle 70a between the first magnet 17a and the second magnet 17b amounts to 90°. However, other higher or lower values are also conceivable.

In order to reduce undesirable interactions of the first magnet 17a and the second magnet 17b, shimming elements 50 may be positioned at the first magnet 17a and the second magnet 17b. The shimming elements 50 may be active shim coils or passive shim irons which may be configured to at least partially encompass the first magnet 17a and the second magnet 17b along a circumferential direction.

FIG. 6 depicts a schematic representation of a magnetic field gradient system 60 of a magnetic resonance imaging system 10 according to the disclosure. The magnetic field gradient system 60 comprises a gradient coil 61 which is positioned on the rotation trajectory 32. The gradient coil 61 may be carried by the magnet holder 33 as shown in FIG. 3 or by a dedicated gradient coil holder 62 as depicted in FIG. 6. The gradient coil holder 62 may be mounted on a carrier element 81 of a mechanical guiding rail 80 as depicted in FIG. 9. It is also conceivable, that the gradient coil 61 is arranged on the magnet 17 as depicted in FIG. 3.

The gradient coil 61 is configured to generate a magnetic gradient field (not shown) which may be used for spatial encoding of magnetic resonance signals acquired from an imaging region 18 within the image acquisition region 14. In one example, the gradient coil 61 is configured to provide a magnetic gradient field oriented along a cranio-caudal direction of the patient 15. The gradient coil 61 may be moved along the rotation trajectory 32 in a unilateral manner. Particularly, the gradient coil 61 may be guided azimuthally along the dental arch 41 of the patient 15.

FIG. 7 holds a schematic representation of a further embodiment of the magnetic field gradient system 60. In this embodiment, the magnetic field gradient system 60 comprises a first gradient coil 61a and a second gradient coil 61b arranged at a 180° angle on the rotation trajectory 32. Thus, the first gradient coil 61a and the second gradient coil 61b may be rotated around the rotation center 31 in a bilateral manner. The gradient coil 61a and the gradient coil 61b may generate a first magnetic gradient field and a second magnetic gradient (not shown) within the image acquisition region 14. It is also conceivable, that the first magnetic gradient field overlaps with the first imaging volume 19a, while the second magnetic gradient field overlaps with the second imaging volume 19b. For this purpose, the angle 70b may correspond to the angle 70a as depicted in FIG. 5. In a further embodiment, the first gradient coil 61a and the second gradient coil 61b may also act as magnetic poles with different magnetic field strengths, thus generating a magnetic gradient field across the entire image acquisition region 14.

In FIG. 8 a further embodiment of the magnetic field gradient system 60 is depicted. In the shown example, the magnetic field gradient system 60 encloses the imaging acquisition region 14 and the jaw region of the patient 15 in a circumferential direction. It is conceivable, that one or more gradient coils, as for example a first gradient coil, a second gradient coil and a third gradient coil, as well as a radiofrequency antenna, are wound around a cylindrical section of the magnetic field gradient system 60. Each gradient coil may be arranged in such a way to at least partially enclose the image acquisition region 14. For example, an arrangement of the gradient coils and/or the radiofrequency antenna may correspond to an arrangement of gradient coils and/or a radiofrequency antenna in a conventional cylindrical magnetic resonance imaging system. The gradient coil 61 depicted in FIG. 8 as well as further gradient coils and/or the radiofrequency antenna may therefore comprise a fixed position with regard to the image acquisition region 14 during a magnetic resonance imaging examination.

FIG. 9 shows a schematic representation of a mechanical guiding rail 80 of a rotation system 30. The representation of the rotation system 30 corresponds to a view that a patient 15 would have, when looking along the Z-direction into the magnetic field generator 13 as depicted in FIG. 1. The guiding rail 80 is embedded in an arc-shaped element 82 of the rotation system 30 and may comprise a perimeter which is positioned parallelly and/or concentrically to the rotation trajectory 32. Thus, a course of the mechanical guiding rail 80 may also be regarded as a rotation trajectory 32. The magnet holder 33 may be carried by a carrier element 81 which is shaped to interlock with a T-shaped groove provided by the mechanical guiding rail 80. The magnet 17 may in turn be carried by the magnet holder 33. As shown in FIG. 9, the magnet 17 is oriented in a direction of the image acquisition region 14. When the carrier element 81 is moved along the mechanical guiding rail 80, the magnet 17 may be moved along the rotation trajectory 32 as shown in FIG. 3. For example, the carrier element 81 may comprise a ball bearing system (not shown) in order to provide a low-friction transport of the magnet holder along the rotation trajectory 32. It is also conceivable, that the carrier element 81 and the magnet holder 33 are driven or moved by a motor (not shown) which may be mounted on the arc-shaped element 82 of the rotation system 30.

FIG. 10 holds a depiction of a magnetic resonance imaging system 10, wherein the first magnet 17a is an electromagnet configured to generate a pulsed first magnetic field inside the imaging volume 19. The pulsed first magnetic field may be configured to pre-polarize nuclear spins inside the imaging volume 19. The second magnet 17b may be an electromagnet or a superconducting magnet configured to generate a homogenous second magnetic field in the imaging volume 19. However, the second magnet 17b may also be permanent magnet. In an exemplary embodiment, the first magnet 17a and the second magnet 17b are moved along the rotation trajectory 32 via the magnet holder 33 in a step-by-step fashion in such a way that magnetic resonance signals can be acquired from the imaging region 18 in each step. However, it is also conceivable, that the second magnet 17b circumferentially encompasses the image acquisition region 14 as well as the head of the patient 15 (not shown). In this case, the second magnet 17b remains in a fixed position while the first magnet 17a is moved along the rotation trajectory 32.

Examples

1. Magnetic resonance imaging system (10) comprising a magnetic field generator (13), an image acquisition region (14) and a radiofrequency system including at least one radiofrequency antenna, wherein the radiofrequency system is configured to emit a radiofrequency excitation pulse into the image acquisition region (14) and receive magnetic resonance signals from the image acquisition region (14), wherein the magnetic field generator (13) comprises:
    at least one magnet (17) configured to generate a magnetic field in the image acquisition region (14),
    a magnet holder (33) configured to carry the at least one magnet (17),
    a rotation system (30) configured to position the magnet holder (33) along a rotation trajectory (32).

2. Magnetic resonance imaging system (10) according to example 1, wherein the magnetic field generator (13) comprises an electromagnet.

3. Magnetic resonance imaging system (10) according to example 1 or 2, wherein the magnetic field generator (13) comprises a permanent magnet.

4. Magnetic resonance imaging system (10) according to example 3, wherein the permanent magnet comprises a C-shaped form and wherein the permanent magnet comprises two magnetic poles positioned at two opposing ends of the C-shaped form.

5. Magnetic resonance imaging system (10) according to example 3, wherein the permanent magnet comprises a bar shape.

6. Magnetic resonance imaging system (10) according to one of the preceding examples, wherein the magnetic field generated by the at least one magnet (17) projects from a face of the poles of the at least one magnet (17) in such way that an imaging volume (19) provided by the at least one magnet (17) is situated in front of the face of the poles.

7. Magnetic resonance imaging system (10) according to one of the preceding examples, wherein the magnetic field generated by the at least one magnet (17) comprises a magnetic field strength in the range of 0.01 to 1.5 Tesla.

8. Magnetic resonance imaging system (10) according to one of the examples 1 to 6, wherein the magnetic field generated by the at least one magnet (17) comprises a magnetic field strength in the range of 0.3 to 1.0 Tesla.

9. Magnetic resonance imaging system (10) according to one of the preceding examples, wherein the at least one magnet (17) is configured to generate a substantially homogeneous magnetic field in the image acquisition region (14).

10. Magnetic resonance imaging system (10) according to one of the examples 1 to 8, wherein the at least one magnet (17) is configured to generate an inhomogeneous magnetic field in the image acquisition region (14) and wherein the inhomogeneous magnetic field comprises a magnetic field gradient along a radial direction of the rotation trajectory (32).

11. Magnetic resonance imaging system (10) according to example 10, further comprising a processor (24) wherein the processor (24) is configured to perform a spatial encoding of magnetic resonance signals acquired from the image acquisition region (14) in dependence of the magnetic field gradient along the radial direction of the rotation trajectory (32).

12. Magnetic resonance imaging system (10) according to one of the preceding examples, wherein the rotation system (30) comprises a mechanical guiding rail (80) which is configured to guide the magnet holder (33) along the rotation trajectory (32) around the rotation center (31).

13. Magnetic resonance imaging system (10) according to one of the preceding examples, wherein the rotation trajectory (32) comprises a rotation angle in the range of 120° to 270.

14. Magnetic resonance imaging system (10) according to one of the examples 1 to 12, wherein the rotation trajectory (32) comprises a rotation angle in the range of 90° to 240°.

15. Magnetic resonance imaging system (10) according to one of the preceding examples, wherein the magnetic field generator (13) comprises a first magnet (17a) and a second magnet (17b), wherein the first magnet (17a) is configured to generate a first magnetic field inside the image acquisition region (14) and the second magnet (17b) is configured to generate a second magnetic field inside the image acquisition region (14).

16. Magnetic resonance imaging system (10) according to example 15, wherein the rotation system (30) is configured to
move the first magnet (17a) from a first end position (37) on the rotation trajectory (32) to a predefined position (39) on the rotation trajectory (32) and
move the second magnet (17b) from the predefined position (39) to a second end position (38) on the rotation trajectory (32).

17. Magnetic resonance imaging system (10) according to one of the examples 15 to 16, wherein the magnetic field generator (13) comprises at least one active shim coil which is configured to reduce undesirable interactions of the first magnetic field and the second magnetic field.

18. Magnetic resonance imaging system (10) according to one of the examples 15 to 16, wherein the magnetic field generator (13) comprises at least one shim iron which is configured to reduce undesirable interactions of the first magnetic field and the second magnetic field.

19. Magnetic resonance imaging system (10) according to one of the preceding examples, wherein the magnetic field generator (13) includes a magnetic field gradient system (60) comprising at least one gradient coil (61), wherein the at least one gradient coil (61) is configured to provide a magnetic gradient field in the image acquisition region (14).

20. Magnetic resonance imaging system (10) according to example 19, wherein the at least one gradient coil (61) is carried by the magnet holder (33).

21. Magnetic resonance imaging system (10) according examples 12 and 19, wherein the rotation system (30) comprises a gradient coil holder (62) configured to carry the at least one gradient coil (61) and wherein the mechanical guiding rail (80) is configured to guide the gradient coil holder (62) along the rotation trajectory (32).

22. Magnetic resonance imaging system (10) according to example 10 and one of the examples 19 to 21, wherein the magnetic gradient field generated by the at least one magnet (17) is oriented at an angle of at least 50°, of at least 70° or at an angle of 90° to the magnetic gradient field generated by the at least one gradient coil (61).

23. Magnetic resonance imaging system (10) according to one of the examples 19 to 22, wherein the magnetic field gradient system (60) comprises a first gradient coil (61a) configured to generate a first magnetic gradient field in the image acquisition region (14) and a second gradient coil (61b) configured to generate a second magnetic gradient field in the image acquisition region (14).

24. Magnetic resonance imaging system (10) according to one of the examples 19 to 23, wherein the processor is configured to perform spatial encoding of magnetic resonance signals acquired from the image acquisition region (14) in dependence of a change of the magnetic field induced by the positioning of the at least one magnet (17) along the rotation trajectory (32) and the magnetic gradient field of the at least one gradient coil (61).

25. Magnetic resonance imaging system (10) according to one of the examples 19 to 23, wherein the magnetic field gradient system (60) comprises a third gradient coil configured to generate a third magnetic gradient field in the image acquisition region (14).

26. Magnetic resonance imaging system (10) according to one of the examples 19 to 25, wherein the magnetic field gradient system (60) comprises two Maxwell coils which are aligned to each other in an angular fashion.

27. Magnetic resonance imaging system (10) according to one of the preceding examples, wherein a contour of the rotation trajectory (32) corresponds to a contour of a body region of a patient (15) and wherein the rotation system (30) is configured to position the magnet holder (33) along the contour of the body region of the patient (15).

28. Magnetic resonance imaging system (10) according to example 27, wherein the contour of the rotation trajectory (32) corresponds to a contour of a jaw region of the patient (15) and wherein the magnetic resonance imaging system (10) is configured to acquire magnetic resonance signals of a tooth and/or a jaw of the patient (15).

29. Magnetic resonance imaging system (10) according to example 27 or 28, wherein the magnetic field generator (13) comprises an adjustment mechanism (12) configured to adjust a position and/or a shape and/or an orientation of the rotation system (30) in order to accommodate for a geometry of the body region of the patient (15).

30. Magnetic resonance imaging system (10) according to one of the examples 27 to 29, wherein a dimension of an imaging region (18) provided by the at least one magnet (17) is lesser than 8 cm in a lateral direction, lesser than 5 cm in a ventrodorsal direction and lesser than 5 cm in a craniocaudal direction.

31. Magnetic resonance imaging system (10) according to one of the examples 27 to 30, wherein the magnetic field generator (13) further comprises a distance adapter (35) configured to adjust a spacing between the magnet holder (33) and a surface (43) of the patient (15).

32. Magnetic resonance imaging system (10) according to example 31, wherein the distance adapter (35) comprises a sensor configured to determine a distance value between the magnet holder (33) and the surface (43) of the patient (15), wherein the distance adapter (35) is configured to adjust a spacing between the magnet holder (33) and the surface (43) of the patient (15) in dependence of the distance value.

33. Magnetic resonance imaging system (10) according to example 31, wherein the radiofrequency system is configured to acquire magnetic resonance navigator data from the image acquisition region (14), wherein the processor is configured to determine a distance value between the magnet holder (33) and the surface (43) of the patient (15) in dependence of the magnetic resonance navigator data and wherein the distance adapter (35) is configured to adjust a spacing between the magnet holder (33) and the surface (43) of the patient (15) in dependence of the distance value.

34. Magnetic resonance imaging system (10) according to example 15, wherein the first magnet (17a) is configured to generate a pulsed first magnetic field and the second magnet (17b) is configured to generate a homogenous second magnetic field, wherein the magnetic resonance imaging system (10) further comprises a controller (20) configured to:
control the first magnet (17a) to generate the pulsed first magnetic field in order to pre-polarize nuclear spins inside an imaging volume (19) and
switch off the first magnet (17a) when the second magnet (17b) is switched on and
control the second magnet (17b) to generate the homogeneous second magnetic field inside the imaging volume (19) during a radiofrequency excitation of the pre-polarized spins and during an acquisition of magnetic resonance signals from the imaging volume (19).

35. Magnetic resonance imaging system (10) according to example 34, wherein the magnetic field strength of the second magnetic field is lower than the magnetic field strength of the pulsed first magnetic field.

36. Magnetic resonance imaging system (10) according to one of the examples 34 to 35, wherein a homogeneity of the second magnetic field is higher than the homogeneity of the pulsed first magnetic field.

CONCLUSION

It shall be understood, that the embodiments described above are to be recognized as examples. Individual embodiments may be extended by features of other embodiments.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:
1. A magnetic resonance imaging (MRI) system comprising:
an image acquisition region;
a radiofrequency system including at least one radiofrequency antenna, the radiofrequency system being configured to emit a radiofrequency excitation pulse into the image acquisition region and receive magnetic resonance signals from the image acquisition region; and a magnetic field generator that includes:
　at least one magnet configured to generate a magnetic field in the image acquisition region;
　a magnet holder configured to carry the at least one magnet; and
　a rotation system configured to position the magnet holder along a rotation trajectory.

2. The MRI system according to claim 1, wherein the at least one magnet is configured to generate an inhomogeneous magnetic field in the image acquisition region, the inhomogeneous magnetic field including a magnetic field gradient along a radial direction of the rotation trajectory.

3. The MRI system according to claim 2, further comprising a controller configured to perform a spatial encoding of magnetic resonance signals acquired from the image acquisition region based on the magnetic field gradient along the radial direction of the rotation trajectory.

4. The MRI system according to claim 1, wherein the rotation system comprises a mechanical guiding rail configured to guide the magnet holder along the rotation trajectory around a rotation center.

5. The MRI system according to claim 1, wherein the rotation trajectory comprises a rotation angle in the range of 120° to 270°.

6. The MRI system according to claim 1, wherein the magnetic field generator comprises:
　a first magnet of the at least one magnet configured to generate a first magnetic field inside the image acquisition region; and
　a second magnet of the at least one magnet configured to generate a second magnetic field inside the image acquisition region.

7. The MRI system according to claim 6, wherein the rotation system is configured to:
　move the first magnet from a first end position on the rotation trajectory to a predefined position on the rotation trajectory; and
　move the second magnet from the predefined position to a second end position on the rotation trajectory.

8. The MRI system according to claim 1, wherein the magnetic field generator comprises a magnetic field gradient system including at least one gradient coil configured to provide a magnetic gradient field in the image acquisition region, the at least one gradient coil being carried by the magnet holder.

9. The MRI system according to claim 4, wherein:
　the magnetic field generator comprises a magnetic field gradient system including at least one gradient coil configured to provide a magnetic gradient field in the image acquisition region; and
　the rotation system comprises a gradient coil holder configured to carry the at least one gradient coil, the mechanical guiding rail being configured to guide the gradient coil holder along the rotation trajectory.

10. The MRI system according to claim 8, wherein the magnetic gradient field generated by the at least one magnet is oriented at an angle of at least 50° to the magnetic gradient field generated by the at least one gradient coil.

11. The MRI system according to claim 8, further comprising a controller configured to perform spatial encoding of magnetic resonance signals acquired from the image acquisition region based on a change of the magnetic field induced by the positioning of the at least one magnet along the rotation trajectory and the magnetic gradient field of the at least one gradient coil.

12. The MRI system according to claim 1, wherein:
　a contour of the rotation trajectory corresponds to a contour of a body region of a patient; and
　the rotation system is configured to position the magnet holder along the contour of the body region of the patient.

13. The MRI system according to claim 12, wherein the contour of the rotation trajectory corresponds to a contour of a jaw region of the patient, the magnetic resonance imaging system being configured to acquire magnetic resonance signals of a tooth and/or a jaw of the patient.

14. The MRI system according to claim 12, wherein the magnetic field generator comprises an adjustment mechanism configured to adjust a position, a shape, and/or an orientation of the rotation system to accommodate for a geometry of the body region of the patient.

15. The MRI system according to claim 12, wherein the magnetic field generator further comprises a distance adapter configured to adjust a spacing between the magnet holder and a surface of the patient.

16. The MRI system according to claim 15, wherein the distance adapter comprises a sensor configured to determine a distance value between the magnet holder and the surface of the patient, the distance adapter being configured to adjust a spacing between the magnet holder and the surface of the patient based on the distance value.

17. The MRI system according to claim 15, wherein:
　the radiofrequency system is configured to acquire magnetic resonance navigator data from the image acquisition region;
　the MRI system further comprises a controller configured to determine a distance value between the magnet holder and the surface of the patient based on the magnetic resonance navigator data; and
　the distance adapter is configured to adjust a spacing between the magnet holder and the surface of the patient based on the distance value.

18. The MRI system according to claim 6, wherein:
　the first magnet is configured to generate a pulsed first magnetic field and the second magnet is configured to generate a homogenous second magnetic field, and
　the magnetic resonance imaging system further comprises a controller configured to:
　　control the first magnet to generate the pulsed first magnetic field to pre-polarize nuclear spins inside an imaging volume and switch off the first magnet when the second magnet is switched on; and
　　control the second magnet to generate the homogeneous second magnetic field inside the imaging volume during a radiofrequency excitation of the pre-polarized spins and during an acquisition of magnetic resonance signals from the imaging volume.

* * * * *